US009839475B2

(12) United States Patent
Solomon et al.

(10) Patent No.: US 9,839,475 B2
(45) Date of Patent: Dec. 12, 2017

(54) HEATED ELEMENT BASED SHAVER WITH HAIR REGROWTH SUPPRESSION

(71) Applicant: Radiancy, Inc., Orangeburg, NY (US)

(72) Inventors: Philip Solomon, Kibbutz Tzora (IL); Dolev Rafaeli, Creskill, NJ (US); Alfred J Intintoli, West Chester, PA (US)

(73) Assignee: ICTV Brands, Inc, Wayne, PA (US)

( * ) Notice: Subject to any disclaimer, the term of this patent is extended or adjusted under 35 U.S.C. 154(b) by 833 days.

(21) Appl. No.: 13/860,577

(22) Filed: Apr. 11, 2013

(65) Prior Publication Data

US 2013/0227841 A1 Sep. 5, 2013

Related U.S. Application Data

(63) Continuation-in-part of application No. PCT/IL2012/050216, filed on Jun. 21, 2012.

(Continued)

(51) Int. Cl.
*A61B 18/18* (2006.01)
*A45D 26/00* (2006.01)
(Continued)

(52) U.S. Cl.
CPC .............. *A61B 18/18* (2013.01); *A45D 26/00* (2013.01); *A45D 26/0009* (2013.01);
(Continued)

(58) Field of Classification Search
CPC combination set(s) only.
See application file for complete search history.

(56) References Cited

U.S. PATENT DOCUMENTS 2,324,148 A * 7/1943 Gravin .................... B26B 21/48
30/140
2,386,409 A * 10/1945 Saffady .................... A01J 23/00
219/233

(Continued)

FOREIGN PATENT DOCUMENTS

JP 2005-211689 8/2005
JP 2005-218824 A 8/2005

(Continued)

OTHER PUBLICATIONS

G.B. Atlshuler; R.R. Anderson; D. Manstein; H.H. Zensie; M.Z. Smirnov; "Extended Theory of Selective Photothermolysis"; Lasers in Surgery and Medicine, vol. 29, pp. 416-432; Published 2001 online by John Wiley & Sons, Inc., Hoboken NJ.

(Continued)

*Primary Examiner* — Anne M Antonucci
*Assistant Examiner* — Renee M Larose
(74) *Attorney, Agent, or Firm* — Simon Kahn; Chanoch Kahn

(57) ABSTRACT

A hair shaving apparatus constitute of: a power source; a control circuitry; a housing, an end of the housing arranged to be juxtaposed to a skin surface; a motion sensor arranged to detect motion of the housing along the skin surface; a hair cutting element secured in relation to the housing, the hair cutting element arranged to be heated to a temperature sufficient to cut hair proceeding from the skin surface; a translation mechanism arranged to translate the hair cutting element between a hair shaving position and a retracted position; and a radiation source, the radiation source responsive to the control circuitry to provide radiation when the motion sensor detects motion in excess of a predetermined minimum quantity, the provided radiation arranged to (Continued)

impact the skin surface for which the hair cutting element is arranged to cut hair with a fluence of at least 0.5 Joules/cm².

19 Claims, 17 Drawing Sheets

Related U.S. Application Data

(60) Provisional application No. 61/499,714, filed on Jun. 22, 2011, provisional application No. 61/499,713, filed on Jun. 22, 2011.

(51) Int. Cl.
  *B26B 21/46* (2006.01)
  *B26B 21/48* (2006.01)
  *A61B 18/20* (2006.01)
  *A61B 18/00* (2006.01)

(52) U.S. Cl.
  CPC ............ *A61B 18/203* (2013.01); *B26B 21/46* (2013.01); *B26B 21/48* (2013.01); *A45D 2026/0095* (2013.01); *A61B 2018/00476* (2013.01)

(56) References Cited

U.S. PATENT DOCUMENTS

| | | | | | |
|---|---|---|---|---|---|
| 2,727,132 | A | * | 12/1955 | Hills | A45D 26/0009 132/212 |
| 3,045,345 | A | * | 7/1962 | Bermingham | B26B 19/42 30/34.2 |
| 3,093,724 | A | * | 6/1963 | Johnson | A45D 26/0009 132/118 |
| 3,176,114 | A | * | 3/1965 | Kneisley | A45D 26/0009 219/223 |
| 3,197,612 | A | * | 7/1965 | Reich | B26B 19/00 19/2 |
| 3,233,322 | A | * | 2/1966 | Sparagi | B26B 21/185 30/41.8 |
| 3,365,797 | A | * | 1/1968 | Cook | B26F 3/06 30/140 |
| 3,406,966 | A | * | 10/1968 | Walton | B65H 15/00 271/176 |
| 3,421,216 | A | * | 1/1969 | Konrad | B26B 19/38 15/1.51 |
| 3,474,224 | A | * | 10/1969 | Carter | A45D 26/0009 219/223 |
| 3,902,042 | A | * | 8/1975 | Goldfarb | B26F 3/12 144/154.5 |
| 3,934,115 | A | * | 1/1976 | Peterson | A45D 26/0009 219/223 |
| 4,051,760 | A | * | 10/1977 | Glennan | B26B 19/24 30/198 |
| 4,130,955 | A | * | 12/1978 | Baumgartner | D06F 75/26 219/257 |
| 4,155,164 | A | * | 5/1979 | White | A61C 7/146 219/227 |
| 4,167,187 | A | * | 9/1979 | Biagi | A61B 18/14 606/36 |
| 4,206,555 | A | * | 6/1980 | Musto | F26B 17/103 34/580 |
| 4,254,324 | A | * | 3/1981 | Vrtaric | A45D 20/12 132/112 |
| 4,498,474 | A | * | 2/1985 | Chalmers | A61B 18/14 606/36 |
| 4,539,467 | A | * | 9/1985 | Wenger | B26D 7/10 219/230 |
| 4,566,454 | A | * | 1/1986 | Mehl | A61B 18/14 606/36 |
| 4,617,926 | A | * | 10/1986 | Sutton | A61B 18/203 385/139 |
| 4,745,260 | A | * | 5/1988 | Albinger, Jr. | D06F 75/26 219/240 |
| 4,819,669 | A | * | 4/1989 | Politzer | A61B 18/203 132/118 |
| 4,940,466 | A | * | 7/1990 | Paduano | A61B 18/14 606/36 |
| 5,021,634 | A | * | 6/1991 | Santoro | G05D 23/2401 219/241 |
| 5,064,993 | A | * | 11/1991 | Hashimoto | A45D 24/10 132/118 |
| 5,065,515 | A | * | 11/1991 | Iderosa | A61B 18/203 132/200 |
| 5,182,857 | A | * | 2/1993 | Simon | A61B 18/203 132/118 |
| 5,197,196 | A | * | 3/1993 | Imagawa | B26B 19/16 249/83 |
| 5,226,907 | A | * | 7/1993 | Tankovich | A45D 26/00 606/131 |
| 5,394,777 | A | * | 3/1995 | Kozikowski | B26B 21/48 30/140 |
| 5,533,266 | A | * | 7/1996 | Kelman | A61B 18/203 132/200 |
| 5,554,838 | A | * | 9/1996 | Berdich | H05B 6/14 219/240 |
| 5,595,568 | A | * | 1/1997 | Anderson | A61B 18/203 606/9 |
| 5,606,798 | A | * | 3/1997 | Kelman | A61B 18/203 219/223 |
| 5,653,025 | A | * | 8/1997 | Cheng | B26B 21/48 30/140 |
| 5,683,380 | A | * | 11/1997 | Eckhouse | A61B 18/203 606/10 |
| 5,820,625 | A | * | 10/1998 | Izawa | A61B 18/203 606/13 |
| 5,871,480 | A | * | 2/1999 | Tankovich | A45D 26/00 606/131 |
| 5,885,273 | A | * | 3/1999 | Eckhouse | A61B 18/203 606/10 |
| 5,925,035 | A | * | 7/1999 | Tankovich | A45D 26/00 606/133 |
| 5,968,034 | A | * | 10/1999 | Fullmer | A61B 18/203 606/13 |
| 5,993,440 | A | * | 11/1999 | Ghassemi | B26B 19/00 30/41.5 |
| 6,032,365 | A | * | 3/2000 | Hodges | B26B 19/14 30/346.51 |
| 6,036,684 | A | * | 3/2000 | Tankovich | A45D 26/00 606/2 |
| 6,043,457 | A | * | 3/2000 | Hashimoto | A45D 26/0009 132/118 |
| 6,045,548 | A | * | 4/2000 | Furumoto | A61B 18/203 606/9 |
| 6,080,146 | A | * | 6/2000 | Altshuler | A61B 18/203 606/12 |
| 6,104,959 | A | * | 8/2000 | Spertell | A61N 5/04 606/31 |
| 6,111,222 | A | * | 8/2000 | Hattori | B23K 3/033 219/240 |
| 6,149,644 | A | * | 11/2000 | Xie | A61B 18/203 606/10 |
| 6,149,645 | A | * | 11/2000 | Tobinick | A61B 18/203 606/10 |
| 6,152,917 | A | * | 11/2000 | Tankovich | A45D 26/00 606/131 |
| 6,187,001 | B1 | * | 2/2001 | Azar | A45D 26/0009 219/223 |
| 6,228,074 | B1 | * | 5/2001 | Almeida | A61B 18/203 606/2 |
| 6,235,015 | B1 | * | 5/2001 | Mead, III | A61B 18/203 606/9 |
| 6,246,027 | B1 | * | 6/2001 | Griffiths | B29C 65/18 132/269 |
| 6,267,771 | B1 | * | 7/2001 | Tankovich | A45D 26/00 128/898 |
| 6,277,129 | B1 | * | 8/2001 | Poran | A45D 26/0023 30/34.05 |

(56) References Cited

U.S. PATENT DOCUMENTS

| | | | | |
|---|---|---|---|---|
| 6,307,181 B1* | 10/2001 | Hashimoto | A45D 26/0009 | 200/553 |
| 6,383,176 B1* | 5/2002 | Connors | A61B 18/203 | 219/223 |
| 6,436,106 B2* | 8/2002 | Yiu | A45D 26/0028 | 606/133 |
| 6,452,501 B1* | 9/2002 | Tse | D06F 75/26 | 200/61.45 R |
| 6,481,104 B1* | 11/2002 | Parker | B26B 21/38 | 30/45 |
| 6,485,484 B1* | 11/2002 | Connors | A61B 18/203 | 606/10 |
| 6,514,243 B1* | 2/2003 | Eckhouse | A61B 18/203 | 606/10 |
| 6,595,985 B1* | 7/2003 | Tobinick | A61B 18/203 | 606/13 |
| 6,641,578 B2* | 11/2003 | Mukai | A61B 18/203 | 606/10 |
| 6,666,856 B2* | 12/2003 | Connors | A61B 18/203 | 606/11 |
| 6,817,101 B1* | 11/2004 | Bohmer | B26B 21/48 | 30/140 |
| 6,824,542 B2* | 11/2004 | Jay | A61B 18/203 | 128/898 |
| 6,825,445 B2* | 11/2004 | Shalev | A45D 26/0009 | 219/223 |
| 6,836,966 B2* | 1/2005 | Patrick | B26B 19/382 | 30/140 |
| 6,976,984 B2* | 12/2005 | Cense | A61B 18/203 | 606/10 |
| 7,029,469 B2* | 4/2006 | Vasily | A61B 18/203 | 128/898 |
| 7,041,094 B2* | 5/2006 | Connors | A61B 18/203 | 606/10 |
| 7,048,746 B2* | 5/2006 | Warden | A61B 17/0467 | 606/138 |
| 7,083,611 B2* | 8/2006 | Lemchen | A61B 18/203 | 128/898 |
| 7,108,690 B1* | 9/2006 | Lefki | A61B 18/203 | 606/10 |
| 7,170,034 B2* | 1/2007 | Shalev | A45D 26/0009 | 219/222 |
| 7,202,446 B2* | 4/2007 | Shalev | A45D 26/0009 | 219/222 |
| 7,204,832 B2* | 4/2007 | Altshuler | A45D 26/0061 | 606/22 |
| 7,217,267 B2* | 5/2007 | Jay | A61B 5/0059 | 128/898 |
| 7,699,058 B1* | 4/2010 | Jay | A61N 5/0617 | 128/898 |
| 8,319,152 B2* | 11/2012 | Shalev | B26B 19/00 | 219/221 |
| 8,367,974 B2 | 2/2013 | Shalev et al. | | |
| 8,389,906 B2 | 3/2013 | Shalev et al. | | |
| 2001/0015016 A1* | 8/2001 | Pragt | B26B 21/00 | 30/34.2 |
| 2001/0053907 A1* | 12/2001 | Ota | A61B 18/203 | 606/10 |
| 2002/0004986 A1* | 1/2002 | Furst | B26B 19/40 | 30/41.5 |
| 2002/0151881 A1* | 10/2002 | Ringler | A61B 18/082 | 606/28 |
| 2003/0032950 A1* | 2/2003 | Altshuler | A61B 17/545 | 606/9 |
| 2003/0036751 A1* | 2/2003 | Anderson | A61B 5/0059 | 606/9 |
| 2003/0037793 A1* | 2/2003 | Hwang | A45D 2/002 | 132/118 |
| 2003/0046816 A1* | 3/2003 | Kanzer | B26B 21/40 | 30/32 |
| 2003/0065314 A1* | 4/2003 | Altshuler | A61B 18/203 | 606/9 |
| 2004/0015156 A1* | 1/2004 | Vasily | A61B 18/203 | 606/9 |
| 2004/0045948 A1* | 3/2004 | Shalev | A45D 26/0009 | 219/223 |
| 2004/0092959 A1* | 5/2004 | Bernaz | A61B 17/54 | 606/131 |
| 2004/0098863 A1* | 5/2004 | Shalev | A45D 26/0009 | 30/140 |
| 2004/0176754 A1* | 9/2004 | Island | A61B 18/203 | 606/9 |
| 2005/0127058 A1* | 6/2005 | Shalev | A45D 26/0009 | 219/223 |
| 2005/0177139 A1* | 8/2005 | Yamazaki | A45D 26/00 | 606/9 |
| 2006/0011024 A1* | 1/2006 | Azar | A45D 26/0009 | 83/13 |
| 2006/0027554 A1* | 2/2006 | Hashimoto | A45D 26/0009 | 219/225 |
| 2006/0070988 A1* | 4/2006 | Shalev | A45D 26/0009 | 219/222 |
| 2006/0293728 A1* | 12/2006 | Roersma | A61N 5/0617 | 607/88 |
| 2007/0016117 A1* | 1/2007 | Sliwa | A45D 26/00 | 601/46 |
| 2007/0084057 A1* | 4/2007 | Shalev | B26B 19/00 | 30/34.2 |
| 2007/0100401 A1* | 5/2007 | Lin | A61B 18/203 | 607/89 |
| 2007/0145031 A1* | 6/2007 | Shalev | A45D 26/0009 | 219/223 |
| 2007/0179490 A1* | 8/2007 | Azar | A61B 18/10 | 606/28 |
| 2008/0215038 A1* | 9/2008 | Bakker | A61B 18/203 | 606/9 |
| 2009/0178281 A1* | 7/2009 | Moore | B26B 21/222 | 30/41.5 |
| 2009/0205208 A1* | 8/2009 | Azar | A45D 26/0009 | 30/34.05 |
| 2009/0211101 A1* | 8/2009 | Azar | A45D 26/0009 | 30/41.6 |
| 2009/0254068 A1* | 10/2009 | Karni | A61B 18/203 | 606/3 |
| 2010/0063565 A1* | 3/2010 | Beerwerth | A61B 18/203 | 607/88 |
| 2010/0198134 A1 | 8/2010 | Eckhouse et al. | | |
| 2011/0166559 A1* | 7/2011 | Eckhouse | A45D 26/00 | 606/9 |

FOREIGN PATENT DOCUMENTS

| | | | |
|---|---|---|---|
| WO | 02/094115 A1 | 11/2002 | |
| WO | 02/094116 A1 | 11/2002 | |

OTHER PUBLICATIONS

G.B. Atlshuler; R.R. Anderson; D. Manstein; H.H. Zenzie; M.Z. Smirnov; "Extended Theory of Selective Photothermolysis"; Lasers in Surgery and Medicine, vol. 29, pp. 416-432; Published 2001 online by John Wiley & Sons, Inc., Hoboken NJ.

* cited by examiner

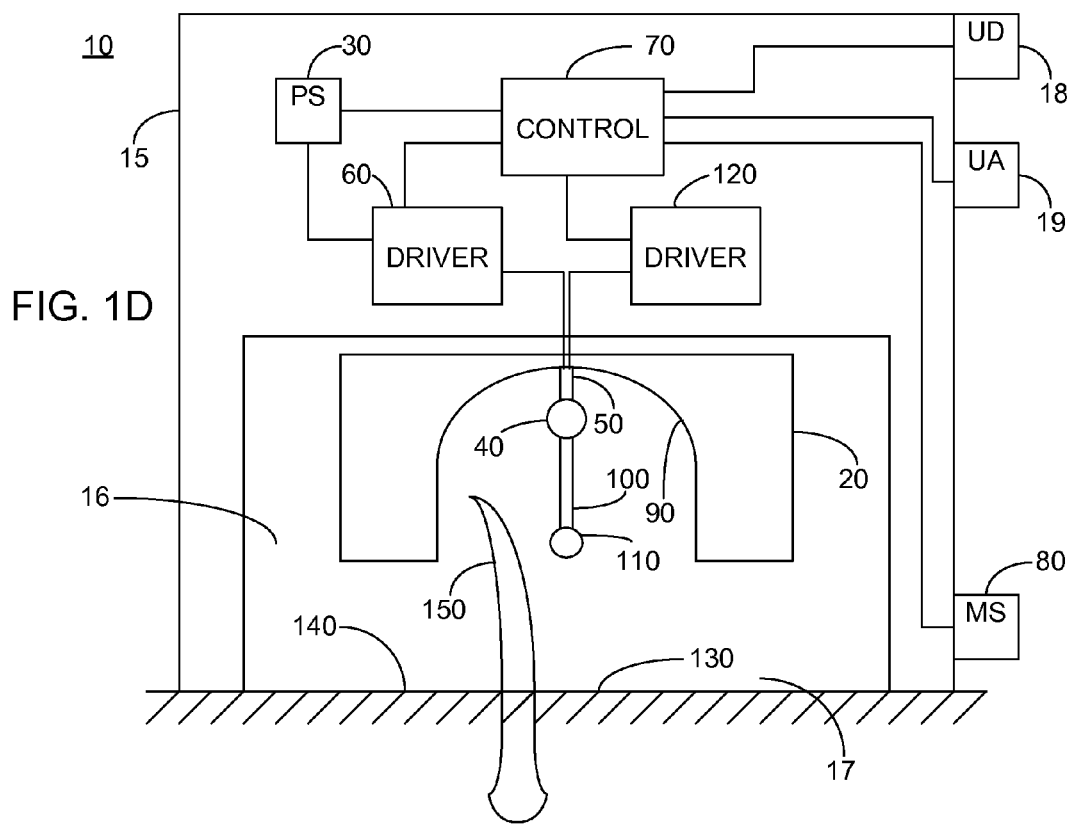

HEATED ELEMENT BASED SHAVER WITH HAIR REGROWTH SUPPRESSION

CROSS-REFERENCE TO RELATED APPLICATIONS

This application is a continuation in part of International Application PCT/IL2012/050216 filed Jun. 21, 2012 published as WO 2013/011505, entitled "Hair Removal and Re-Growth Suppression Apparatus, which claims priority from: U.S. Provisional Patent Application Ser. No. 61/499,714 filed Jun. 22, 2011 entitled "MODIFIED HOME USE HAIR REMOVAL DEVICE"; and U.S. Provisional Patent Application Ser. No. 61/499,713 filed Jun. 22, 2011 entitled "HAIR TREATMENT AND REMOVAL APPARATUS". The entire contents of each of the above are incorporated herein by reference.

TECHNICAL FIELD

The present invention relates generally to the field of hair removal and more particularly to a hair shaving apparatus with a heating element supplemented with an irradiation source for hair regrowth suppression.

BACKGROUND

The removal of unwanted hair growth from the body can be accomplished with mechanized means, for example razors, tweezers or wax, all of which are uncomfortable to use, irritate the skin and/or cause damage to the skin. Another form of hair removal is by heating the hair growth to a temperature sufficient to cut the hair, however a concern of devices for hair removal involving heat is the danger of skin damage from excess heat. U.S. Pat. No. 6,825,445, issued Nov. 30, 2004 to Shalev et al., the entire contents of which is incorporated herein by reference, is addressed to an electric shaver comprising a heat generator and one or more heat elements heated to a temperature sufficient to cut hair, the heat generator arranged to prevent heat from being applied continuously in a single area for sufficient time to cause skin damage.

U.S. Pat. No. 7,170,034, issued Jan. 30, 2007 to Shalev et al., the entire contents of which is incorporated herein by reference, is addressed to an electric shaver comprising a heat element heated to a temperature sufficient to cut hair, the heating of the heat element being pulsed to prevent heat from being applied continuously in a single area for sufficient time to cause skin damage.

U.S. Pat. No. 7,202,446, issued Apr. 10, 2007 to Shalev et al., the entire contents of which is incorporated herein by reference, is addressed to an electric shaver comprising an elongated element heated to a temperature capable of cutting hair and a vibrating structure on which the elongated element is mounted, the vibrating structure arranged to prevent skin damage.

U.S. published patent application Ser. No. 2009/0205208 published Aug. 20, 2009 to Shalev, et al, the entire contents of which is incorporated herein by reference, is addressed to a hair cutting device comprising a detector adapted to detect motion of the shaver heated wire arranged to cut hair, a hair cutting removal and suppression head having a heated wire suitable for heating hair growing from the skin and cutting the hair, and a controller arranged to move the hair cutting removal and suppression head between a hair cutting position and a retracted position responsive to the presence of, or absence of, detected motion.

It is known that heating hair follicles affects hair growth rate. Experience has shown that repeated use of heat based hair removal devices, such as certain products available commercially from Radiancy, Inc. of Orangeburg, New York, reduces hair growth rate. Although hair growth rate is reduced by the above mentioned products, hair growth rate reduction is achieved as a byproduct, and is thus not optimal.

Follicular epithelial stem cells (FESC) are present within 0.5 mm of the skin surface in non-scalp skin. There is evidence that permanent thermal damage to FESCs are not specifically necessary to change the cell signaling between the FESC and the associated papilla, or that FESC are even involved in the induction of a catagen-like state that shuts down hair growth after injury to follicles. However, it is well known in medicine that subtle damage and stimuli can induce long-lasting biological inhibition in hair growth. These stimuli include mild hyperthermia; for example, fever can induce telogen effluvium, the loss of hair due to induction of catagen phase (the transitional phase between anagen and telogen lasting about 3 to 6 weeks). Other stimuli include hypoxia, oxidative stress, toxic chemical exposure, antimetabolites and radiation. The anagen (actively growing) hair follicle is ready to undergo apoptosis and its transition to telogen (resting) upon a number of triggers. This transition would not cause permanent hair loss, but would lead to long-lasting hair growth suppression, especially if the injury or stimuli were repeated frequently.

It would be desirable therefore to provide the benefits of such a long lasting hair growth suppression in cooperation with a shaver.

SUMMARY

Accordingly, it is a principal object to overcome at least some of the disadvantages of prior art. This is accomplished in certain embodiments by providing an integrated device comprising a shaver utilizing a cutting element and an irradiating element arranged to irradiate a skin portion with light sufficient to provide hair growth suppression. Preferably such light is arranged to provide thermal stimuli to a depth of 0.5 to about 1 mm below the skin inducing a catagen-like state of the hair follicles. In one embodiment, the cutting element is a heated element and in another embodiment the cutting element and irradiating element are provided as a unitary element. In an exemplary embodiment, the light source is arranged to provide a fluence of 0.5 to 2 Joules/cm$^2$ to the skin portion.

In one embodiment, the light source is a broadband halogen lamp arranged to emit light in wavelengths between 400 nanometers and 1100 nanometers. In one further embodiment, the lamp is arranged to emit light predominantly in wavelengths between 500 nanometers and 900 nanometers.

In one embodiment the light source is arranged to provide the light in a round spot on the skin portion.

In one embodiment, the light source is a light emitting diode (LED) arranged to emit light in wavelengths between 430 nanometers and 1070 nanometers. In one further embodiment, the light source is an array of LEDs, optionally arranged to produce an elongated illumination zone of the skin portion.

In one embodiment, the light source is a laser diode arranged to emit light in a wavelength between 430 nanometers and 1070 nanometers. In one further embodiment, the light source is an array of laser diodes, optionally arranged to produce an elongated illumination zone of the skin portion. In yet another embodiment, a scanning optical element is provided in optical communication with the light source, the scanning optical element arranged to form a predetermined shaped illumination zone shaped on the skin portion.

In one embodiment, a motion sensor and a control circuit are provided, the control circuit arranged to adjust the intensity of light impinging on the skin portion responsive to the amount of detected motion by the motion sensor.

Additional features and advantages will become apparent from the following drawings and description.

BRIEF DESCRIPTION OF THE DRAWINGS

For a better understanding of the invention and to show how the same may be carried into effect, reference will now be made, purely by way of example, to the accompanying drawings in which like numerals designate corresponding elements or sections throughout.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. In the accompanying drawings:

FIGS. 1A-1G illustrate a plurality of views of various components of a hair removal and re-growth suppression apparatus comprising an irradiating element and a cutting element, according to certain embodiments;

DETAILED DESCRIPTION OF THE PREFERRED EMBODIMENTS

Figure 1A:
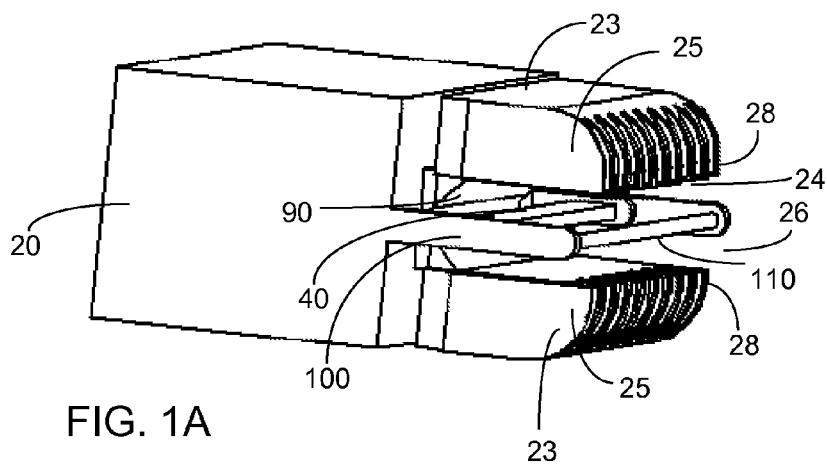
Figure 1B:
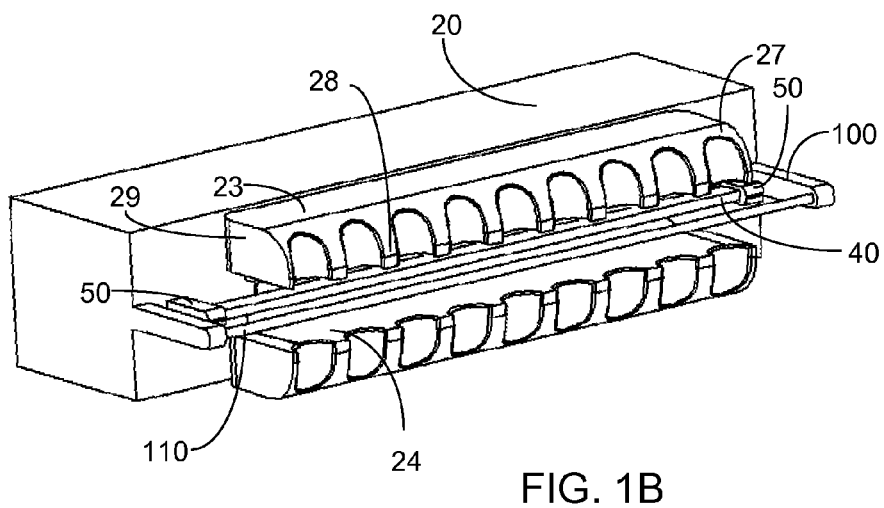
Figure 1C:
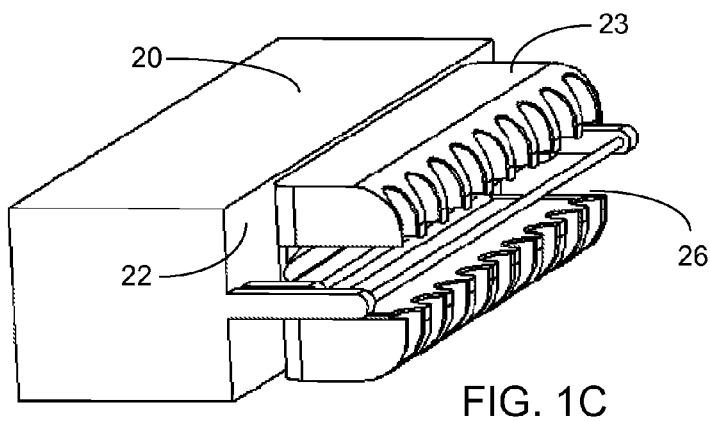

Before explaining at least one embodiment of the invention in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting.

Figure 1F:
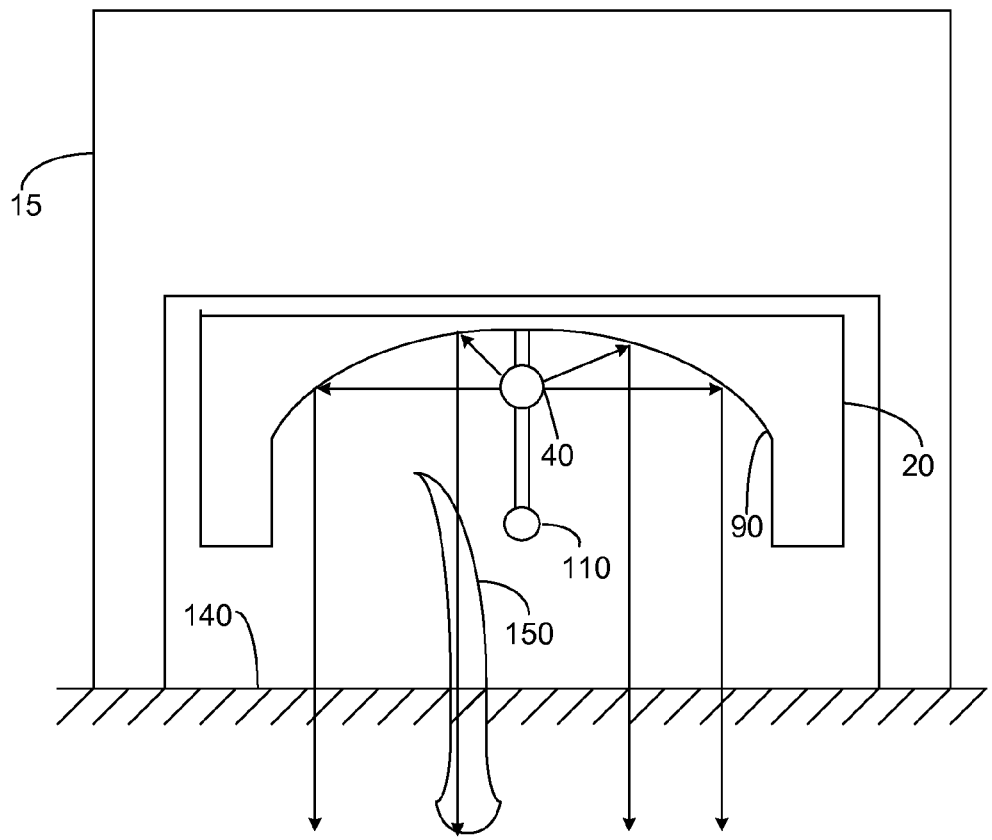
Figure 1G:
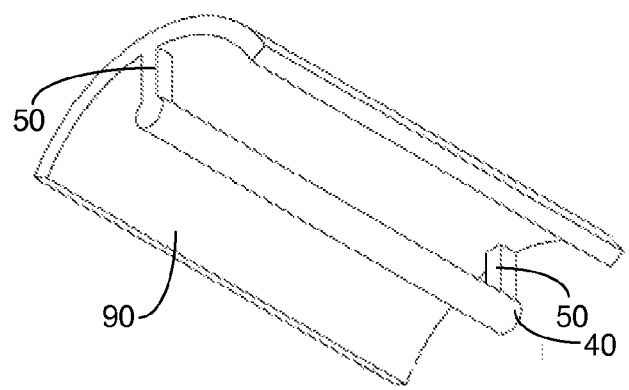

FIGS. 1A-1G illustrate a plurality of views of various components of a hair removal and re-growth suppression apparatus 10. Specifically, FIGS. 1A-1C each illustrate an isometric view of a removal and suppression head 20 of hair removal and re-growth suppression apparatus 10; FIGS. 1D-1F each illustrate a high level side cut view of hair removal and re-growth suppression apparatus 10; and FIG. 1G illustrates an isometric view of an irradiating element 40 and a reflector 90, according to certain embodiments. FIG. 1D further illustrates a high level schematic drawing of certain electrical components of hair removal and re-growth suppression apparatus 10. FIGS. 1A-1G will be described together. Hair removal and re-growth suppression apparatus 10 comprises: a housing 15, exhibiting an opening 17; a user input device 18; a user alarm 19; a removal and suppression head 20 exhibiting a wall 22; an extender assembly 23, constituted of a pair of arms 25, extender assembly 23 exhibiting a first end 27, a second end 29 and a longitudinal end 28; a power source 30; an irradiating element 40; a pair of first connectors 50; a driver 60; a control circuitry 70; a motion sensor 80; reflector 90; a pair of second connectors 100; a cutting element 110; and a driver 120.

In one non-limiting embodiment, user input device 18 comprises one of a push button, a touch screen and a switch. In one non-limiting embodiment, user alarm 19 comprises one of an LED, an audible alarm and a screen display. In one embodiment, extender assembly 23 exhibits low thermal conductivity. In one embodiment, extender assembly 23 is composed of a ceramic material. In one embodiment, longitudinal end 28 of extender assembly 23 comprises a plurality of teeth, thereby providing minimal surface area. In one embodiment, an inner face 24 of extender assembly 23 is constituted of reflective material arranged to substantially reflect EMR exhibiting wavelengths of 500-5000 nm. In one embodiment, each face 24 is constituted of aluminum oxide, in one further embodiment the purity of the aluminum oxide being between 90-99.5%. In one embodiment, the reflectivity of each face 24 is at least 96% at 500 nm and 98% at 1000 nm. In one embodiment, the reflective surface of each face 24 is substantially smooth. In one embodiment, power source 30 is arranged to be connected via a power cord to a power mains. In one embodiment, power source 30 is a rechargeable power source.

In one embodiment, irradiating element 40 comprises a wire. In another embodiment, irradiating element 40 comprises a ribbon. In one embodiment, irradiating element 40 comprises a Nickel Chromium alloy. In one further embodiment, irradiating element 40 comprises Nichrome. In another embodiment, irradiating element 40 comprises a Molybdenum disilicide alloy. In another embodiment, irradiating element 40 comprises a ferritic iron-chromium-aluminum alloy. In one embodiment, irradiating element 40 is arranged to output EMR exhibiting about 95% of its energy within a spectrum of between 500-5000 nm, in one particular embodiment the EMR exhibiting less than 10% of its energy within a spectrum of between 500-1000 nm. In one embodiment, the output EMR exhibits about 95% of its energy around a wavelength of 1000 nm. In one embodiment, irradiating element 40 is arranged to be heated up to a temperature of 400°-1900° C. responsive to an appropriate current flowing there through. In one particular embodiment, irradiating element is arranged to be heated up to a temperature of 1000°-1900° C. and in one further embodiment to a temperature of about 1900° C., responsive to an appropriate current flowing there through. In another embodiment, irradiating element 40 is arranged to be heated to a temperature of greater than 1900° C. In one embodiment, irradiating element 40 is elongated square cuboid shaped. In another embodiment, irradiating element 40 is elongated rectangular cuboid shaped. In one embodiment, the length of irradiating element 40 is between 1-100 times longer than the width thereof. In one particular embodiment, the length of irradiating element 40 is 5 times longer than the width thereof. In another embodiment, the length of irradiating element 40 is more than 100 times longer than the width thereof. In another embodiment, as illustrated in FIG. 1D, irradiating element 40 is cylindrically shaped.

In one embodiment, a first connector of first connector pair 50 and a first connector of second connector pair 100 are constituted of a single unified connector and a second connector of first connector pair 50 and a second connector of second connector pair 100 are constituted of a single unified connector.

In one embodiment, driver 60 and driver 120 are provided as a single driver. In one embodiment, driver 60 is a current driver and in another embodiment driver 60 is a voltage driver. In one embodiment, driver 120 is a current driver and in another embodiment driver 120 is a voltage driver. In one embodiment, motion sensor 80 comprises any of a plurality of standard motion sensors including, but not limited to: an optical sensor; a magnetic sensor; a mechanical sensor; and an ultrasonic sensor. In one particular embodiment, motion sensor 80 comprises a roller arranged to come in contact with a skin surface. Control circuitry 70 is arranged to calculate the rate of relative motion of housing 15 along a skin surface 140 responsive to motion sensor 80. In one embodiment, as illustrated in FIG. 1D, reflector 90 is elongated concave shaped. In another embodiment, as illustrated in FIG. 1E, reflector 90 is elongated v-shaped. In another embodiment, reflector 90 is elongated open trapezoid shaped. In another embodiment, reflector 90 is elongated paraboloid shaped.

In one embodiment, reflector 90 is constituted of reflective material arranged to substantially reflect EMR exhibiting wavelengths of 500-5000 nm. In one embodiment, reflector 90 is constituted of aluminum oxide, in one further embodiment the purity of the aluminum oxide being between 90-99.5%. In one embodiment, the reflectivity of reflector 90 is at least 96% at 500 nm and 98% at 1000 nm. In one embodiment, the reflective surface of reflector 90 is substantially smooth. In one embodiment, the thermal conductivity of reflector 90 is about 35 W/mK°, thus providing for superior heat transfer characteristics.

In one embodiment, cutting element 110 comprises an elongate shaped wire. In another embodiment, cutting element 110 comprises a ribbon. In one further embodiment, cutting element 110 comprises a Nickel Chromium alloy. In one further embodiment, cutting element 110 comprises Nichrome. In another embodiment, irradiating element 40 comprises a Molybdenum disilicide alloy. In another embodiment, irradiating element 40 comprises a ferritic iron-chromium-aluminum alloy. In one embodiment, cutting element 110 is arranged to be heated to a temperature of 400°-1900° C., responsive to an appropriate current flowing therethrough. In one particular embodiment, cutting element 110 is arranged to be heated to a temperature of 1000°-1900° C., responsive to an appropriate current flowing therethrough. Optionally, a thermal sensor is provided (not shown) in communication with cutting element 110, the output of the thermal sensor provided as a feedback to control circuitry 70. In such an embodiment, control circuitry 70 is arranged to maintain supervisory control of the temperature of cutting element 110 and prevent the temperature of cutting element 110 from exceeding a predetermined maximum, and optionally further ensure that the temperature of cutting element 110 does not fall below a predetermined minimum during operation.

Extender assembly 23 extends outward from a particular location on wall 22 of removal and suppression head 20 towards longitudinal end 28, and is arranged to meet a portion 130 of skin surface 140. In one embodiment, extender assembly 23 is constituted of a pair of parallel arms 25, displaced one from the other, with inner faces 24 facing each other. Parallel arms 25 form an opening 26 between longitudinal ends 28. In one embodiment (not shown), extender assembly 23 comprises opposing walls of an enclosure extending outward from wall 22 of removal and suppression head 20 towards longitudinal end 28.

One of first connectors 50 extends outward from wall 22 of removal and suppression head 20, facing the opening between parallel arms 25 at first ends 27. Another of first connectors 50 extends outward from wall 22 of removal and suppression head 20, facing the opening between parallel arms 25 at second ends 29. One of second connectors 100 extends outward from wall 22 of removal and suppression head 20, facing the opening between parallel arms 25 at first ends 27. Another of second connectors 100 extends outward from removal and suppression head 20 facing the opening between parallel arms 25 at second ends 29.

Each end of irradiating element 40 is connected to a particular first connector 50. In one embodiment, where irradiating element 40 is elongated rectangular cuboid shaped, the edge of irradiating element 40 facing wall 22 of removal and suppression head 20, and the edge parallel thereto, are narrower than the edges parallel to parallel arms 25. In another embodiment (not shown), where irradiating element 40 is elongated rectangular cuboid shaped, the edge of irradiating element 40 facing wall 22 of removal and suppression head 20, and the edge parallel thereto, are wider than the edges parallel to parallel arms 25. In one embodiment, the distance between irradiating element 40 and opening 26 is between 0.1-80 mm. Reflector 90 is, in one embodiment, disposed on removal and suppression head 20 between parallel arms 25 and fixed in relation to wall 22. In one embodiment, the walls of reflector 90 extend past irradiating element 40 towards opening 26. In one embodiment, a plurality of reflectors 90 are provided and disposed on faces 24 of parallel arms 25.

Each end of cutting element 110 is connected to a particular second connector 100. In one embodiment, cutting element 110 is situated between irradiating element 40 and opening 26. In one embodiment, cutting element 110 is displaced from opening 26, in the direction of wall 22 of removal and suppression head 20, by less than 5 mm, in one particular embodiment the displacement is less than 3 mm. In one non-limiting embodiment, irradiating element 40 and cutting element 110 are parallel to each other within a plane perpendicular to opening 26.

In one embodiment, power source 30, driver 60, control circuitry 70 and driver 120 are situated within housing 15. Removal and suppression head 20 is situated within a cavity 16 of housing 15 formed by opening 17, with opening 26 of removal and suppression head 20 facing opening 17 of housing 15. A first input of control circuitry 70 is connected to an output of motion sensor 80 and a second input of control circuitry 70 is connected to an output of power source 30. A power input of driver 60 is connected to a respective output of power source 30 and a control input of driver 60 is connected to a respective output of control circuitry 70. An output of driver 60 is connected to irradiating element 40. In one embodiment, driver 60 is connected to irradiating element 40 via pair of first connectors 50. A power input of driver 120 (not shown) is connected to a respective output of power source 30 and a control input of driver 120 is connected to a respective output of control circuitry 70. An output of driver 120 is connected to cutting element 120. In one embodiment, driver 120 is connected to cutting element 110 via pair of second connectors 100. An output of user input device 18 is connected to a third input of control circuitry 70 and an input of user alarm 19 is connected to a respective output of control circuitry 70.

In one embodiment, the connection of removal and suppression head 20 to housing 15 is such that removal and suppression head 20 can be detached from housing 15 by a user and replaced with a different removal and suppression head 20.

In operation, a portion of opening 17 of housing 15 is juxtaposed with portion 130 of skin surface 140, in one embodiment by a user grasping housing 15. Responsive to a user input at user input device 18, control circuitry 70 controls driver 60 to drive current through irradiating element 40, thereby irradiating element 40 begins to produce electromagnetic radiation (EMR), as a result of the heating thereof, which is radiated in a plurality of directions. In one embodiment, a portion of the heat and EMR is radiated in the direction of opening 26 and a majority of the heat and EMR is radiated in the direction of reflector 90. EMR is reflected off reflector 90 in the general direction of opening 26. Thus, a large portion of the EMR radiated from irradiating element 40 reaches portion 130 of skin surface 140 via opening 26 and radiates the hair follicles, and/or the inner skin layers, under portion 130 of skin surface 140. The EMR penetrating skin surface 140 is preferably of a wavelength arranged to be absorbed by hair follicles and/or the matter in the immediate surroundings thereof, thereby heating the hair follicles, while providing minimal absorption by the epidermis. In one embodiment, the EMR is arranged to induce a catagen-like state of the hair follicle, while limiting heating of the epidermis so as not to cause damage thereto. In one embodiment, irradiating element 40 and reflector 90 are arranged such that the EMR output by irradiating element 40 is reflected so as to be focused along a line parallel to irradiating element 40, at a depth of 0.5-10 mm beneath skin surface 140. In one embodiment, irradiating element 40 and reflector 90 are arranged such that the EMR is focused along lines generally perpendicular to portion 130 of skin surface 140 so as to maximize penetration of skin and reduce reflection of the EMR off skin surface 140.

In one embodiment, driver 60 is arranged to drive irradiating element 40 to output EMR with a power between 0.5-20 W, in one particular embodiment with a power between 1-10 W. In one embodiment, driver 60 is arranged to drive irradiating element 40 to output EMR with fluence between 0.5-10 J/cm$^2$, measured at opening 26, in one particular embodiment the fluence being about 3 J/cm$^2$. In another embodiment, driver 60 is arranged to drive irradiating element 40 to output EMR with fluence between 0.5-2 J/cm$^2$, measured at opening 26, in one particular embodiment the fluence being about 1 J/cm$^2$.

A very small portion of the energy of the EMR is within the ultraviolet (UV) spectrum of less than 400 nm. Thus, minimal harmful UV radiation reaches the skin and no UV filters are required. Furthermore, radiation with wavelengths greater than 1000 nm, i.e. infrared (IR) radiation, is less susceptible to scattering and reflecting off the skin. Additionally, IR radiation is less absorbed and better in reaching the deeper layers of skin, such as the dermis, than radiation with wavelengths less than 1000 nm. Advantageously, the EMR radiation within the spectrum of between 500-1000 nm, because of the melanin in the epidermis and hair follicle, preferably provides thermal stimuli to a depth of 0.5 to about 1 mm below the skin inducing a catagen-like state of the hair follicles.

Heat radiated from irradiating element 40 in the direction of reflector 90, representing the majority of the heat output by irradiating element 40, is absorbed thereby and in one embodiment is conducted and/or transferred by convection through reflector 90. Heat radiated from irradiating element 40 in the directions of first ends 27 and second ends 29 of extender assembly 23 exits the openings there between. Thus, only a small portion of the heat radiated by irradiating element 40 reaches portion 130 of skin surface 140. In particular, in the embodiment where irradiating element 40 is rectangular cuboid shaped, the majority of the heat output by irradiating element 40 reaches reflector 90 and only a small portion reaches opening 26. Since only a small portion of the output heat reaches portion 130 of skin surface 140, any risk associated with a rise in the temperature of the skin (e.g. burn) is limited. In one embodiment, as will be described below in relation to FIGS. 8A and 9, one or more heat vents are provided, arranged to vent excess heat away from skin surface 140.

In order to perform shaving, or other hair cutting, the user moves removal and suppression head 20 along skin surface 140. In one embodiment, responsive to an output of motion sensor 80 indicative that housing 15 is in relative motion in relation to skin surface 140 with a rate of motion greater than a predetermined first minimum, control circuitry 70 is arranged to control driver 120 to drive current through cutting element 110, thereby cutting element 110 produces heat. In one embodiment, a mechanical positioning mechanism (not shown) is further supplied to move cutting element 110 to a position adjacent skin surface 140, optionally to a distance of less than 3 mm from skin surface 140. In one embodiment, current is driven through irradiating element 40 by control circuitry 70 only when current is driven through cutting element 110. In another embodiment, current is driven through irradiating element 40 irrespective of the output of motion sensor 80. In yet another embodiment, current is driven through irradiating element 40 responsive to a rate of relative motion sensed by motion sensor 80 exceeding a first limit, and current is driven through cutting element 110 responsive to a rate of relative motion sensed by motion sensor 80 exceeding a second limit, the second limit greater than the first limit. A hair 150, protruding from portion 130 of skin surface 140, comes in contact with cutting element 110 and is cut by heated cutting element 110, such as by singeing. Advantageously, the diameter of cutting element 110 is small enough such that heat output thereby is substantially dissipated before reaching portion 130 of skin surface 140. Furthermore, a small diameter of cutting element 110 is advantageous so as to provide a low thermal mass for cutting element 110, thus preventing unintended burning of skin surface 140 when the rate of relative motion drops below the predetermined limit of operation and cutting element 110 is de-energized. In one embodiment, the diameter of cutting element 110 is between 10-300 μm.

In one embodiment, in the event motion sensor 80 detects that the rate of relative motion of housing 15 is below a predetermined limit, control circuitry 70 is arranged to control driver 120 to cease current flow through cutting element 110. Optionally, current is similarly ceased by driver 60 through irradiating element 40. In one preferred embodiment, as will be described below in relation to FIGS. 2A-2B removal and suppression head 20 is translated away from the skin. In another embodiment, cutting element 110 is translated away from the skin with no translation of removal and suppression head 20. In one embodiment, user alarm 19 outputs an indicator that the rate of relative motion of housing 15 should be increased. Alternately, as described above, different limits are supplied for each of driver 60 and driver 120. Thus, a rate of relative motion less than the above mentioned second limit results in a cessation of current to cutting element 110, with an optional motion of cutting element 110 away from skin surface 140, and a rate of relative motion less than the above mentioned first limit results in a cessation of current to irradiating element 140 with an optional motion of irradiating element away from skin surface 140. Alternately, current through irradiating element 40 is a function of the detected rate of relative motion, and a range of output radiation is supplied by irradiating element 40 responsive to the value of the detected rate of relative motion. In one embodiment, the control of current through each of irradiating element 40 and cutting element 110 is controlled such that the temperature of portion 130 of skin surface 140, when juxtaposed with opening 26, is 40°-46° C.

In another embodiment, in the event motion sensor 80 detects no motion of housing 15, or relative motion below a predetermined safety threshold, control circuitry 70 controls one or both of drivers 60, 120 to interrupt the current flow through the respective one of irradiating element 40 and cutting element 110. In one preferred embodiment, as will be described below in relation to FIGS. 2A-2B, removal and suppression head 20 is translated away from the skin. In another embodiment, cutting element 110 is translated away from the skin with no translation of removal and suppression head 20. Preferably, in the event that no relative motion is detected for a predetermined time period, control circuitry 70 is arranged to control driver 60 to interrupt current flow through irradiating element 40 and control driver 120 to interrupt current flow through cutting element 110. In one embodiment, user alarm 19 outputs an indicator that the rate of relative motion of housing 15 should be increased.

In one embodiment, control circuitry 70 is arranged to control driver 60 to pulseably drive current through irradiating element 40. In the embodiment where control circuitry 70 is arranged to calculate the rate of relative motion of housing 15 over skin surface 140 responsive to input from the detection of motion sensor 80, optionally the duty cycle of driver 60 is a function of the detected rate of relative motion. As the rate of relative motion of housing 15 increases, the duty cycle of driver 60 increases and as the rate of relative motion of housing 15 decreases, the duty cycle of driver 60 decreases. In one embodiment, the duty cycle of driver 60 is adjusted such that the temperature of portion 130 of skin surface 140, when juxtaposed with opening 26, is 40°-46° C. In one embodiment, the duty cycle of driver 60 is adjusted to provide a pulse length of:

$$T = X/V \quad \text{EQ. 1}$$

where X is the spacing between longitudinal ends 28 of parallel arms 25, defining opening 26, and V is the detected rate of relative motion of housing 15.

In one embodiment, control circuitry 70 is arranged to control driver 120 to pulseably drive current through cutting element 110. In the embodiment where control circuitry 70 is arranged to calculate the rate of relative motion of housing 15 over skin surface 140 responsive to the detection of motion sensor 80, optionally the duty cycle of driver 110 is a function of the detected rate of relative motion. As the rate of relative motion of housing 15 increases, the duty cycle of driver 110 increases and as the rate of relative motion of housing 15 decreases, the duty cycle of driver 110 decreases.

The above has been described in an embodiment where cutting element 110 is a heated element, however this is not meant to be limiting in any way. In another embodiment, cutting element 110 is provided as a blade arranged to cut hair which comes in contact therewith during motion of removal and suppression head 20 in relation to the hair.

Figure 2A:
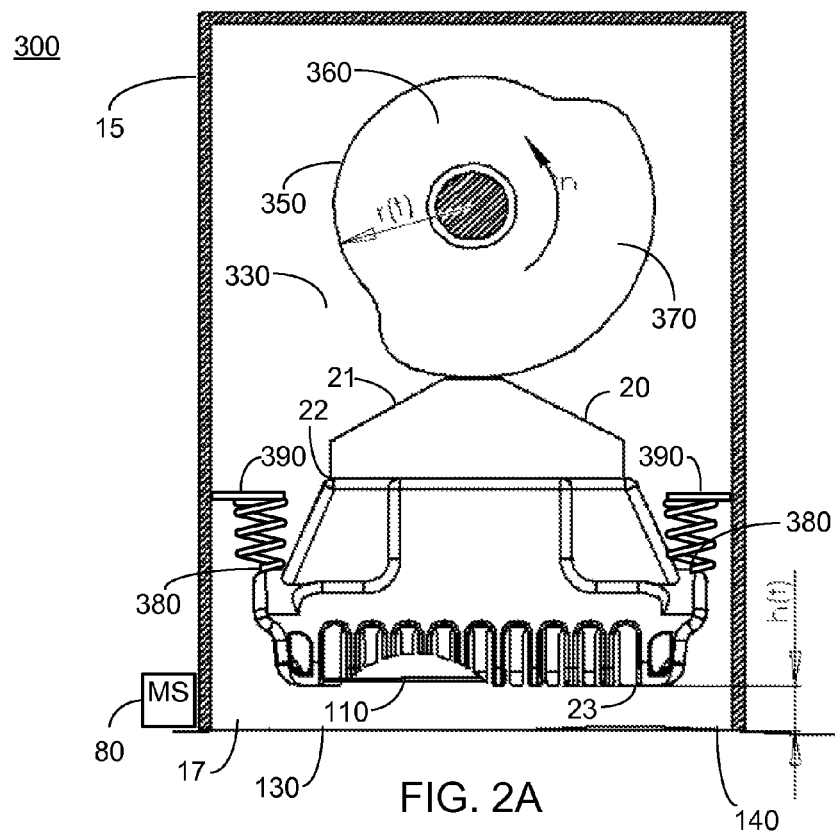
FIG. 2A illustrates a high level side cut view of the hair removal and re-growth suppression apparatus of FIGS. 1A-1G, further comprising a regular translation mechanism, according to certain embodiments.
Figure 2B:
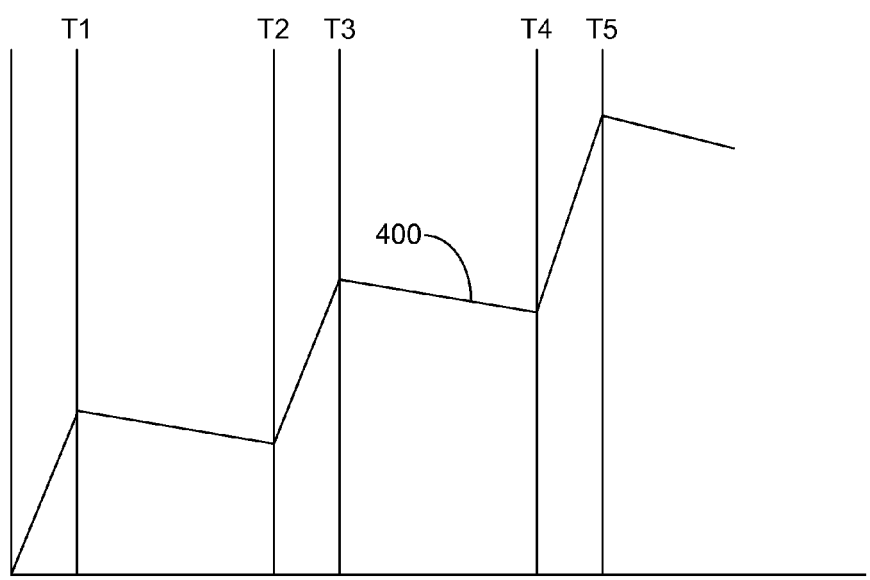
FIG. 2B illustrates a graph showing the effect of the hair removal and re-growth suppression apparatus of FIG. 2A on the temperature of the epidermis.

FIG. 2A illustrates a high level side cut view of a hair removal and re-growth suppression apparatus 300 and FIG. 2B illustrates a graph showing the effect of the operation of hair removal and re-growth suppression apparatus 300 on the epidermis and hair follicles, wherein the x-axis represents time and the y-axis represents temperature, both in arbitrary units, the figures being described together. Hair removal and re-growth suppression apparatus 300 is in all respects similar to hair removal and re-growth suppression apparatus 10 of FIGS. 1A-1E, and further comprises a translation mechanism 330. In one embodiment reflector 90 is not provided. In one embodiment (not shown), motion sensor 80 is not provided. For the sake of simplicity, user input device 18, user alarm 19, power source 30, irradiating element 40, driver 60, control circuitry 70 and driver 120 are not shown. In one non-limiting embodiment, translation mechanism 330 comprises: a cam 350, exhibiting a shortened radius portion 360 and an extended radius portion 370; a plurality of springs 380; and a plurality of spring connectors 390. In one embodiment (not shown), cam 350 comprises a plurality of mechanical parts allowing for adjustment of shortened radius portion 360 and extended radius portion 370. In another embodiment (not shown), translation mechanism 330 comprises a mechanical cradle. In another embodiment (not shown), translation mechanism 330 comprises a swinging lever arranged for alternate rectilinear motion.

Each spring 380 is connected at one end to removal and suppression head 20 and at a second end to housing 15, via a respective spring connector 390. A wall 21 of removal and suppression head 20, opposing wall 22 of removal and suppression head 20 and displaced thereof away from opening 17 of housing 15, is arranged to come in contact with cam 350. Cam 350 is rotated by a motor (not shown), which is in communication with control circuitry 70 and power source 30.

In operation, a portion of opening 17 of housing 15 is juxtaposed with portion 130 of skin surface 140, in one embodiment by a user grasping housing 15. Initially, responsive to a user input at user input device 18, extended radius portion 370 of cam 350 comes in contact with removal and suppression head 20, thereby removal and suppression head 20 is translated to a treatment position in relation to opening 17 of housing 15, the treatment position also known herein as the first position. In one embodiment, in the treatment position, the distance between cutting element 110 and opening 17, denoted h(t), is less than 3 mm, and in one particular embodiment is between 0.1-1 mm. In another embodiment, in the treatment position, cutting element 110 is level with opening 17 of housing 15. Control circuitry 70 controls drivers 60 and 120 to drive current through irradiating element 40 (not shown) and cutting element 110, respectively. As described above, heat and EMR is output from irradiating element 40, with radiation reaching portion 130 of skin surface 140 and preferably absorbed by melanin in the epidermis and in the hair follicles therein. Heat is output from cutting element 110, arranged to cut any hair portions in contact therewith, as described above. Additionally, control circuitry 70 is arranged to control cam 350 to begin to rotate. Curve 400 of FIG. 2B represents the temperature of the epidermis of portion 130 of skin surface 140. As shown by curve 400, the temperature of the epidermis, are impacted with each successive treatment by increasing temperature over time. The increasing temperature provides the thermal stimuli inducing the catagen-like state of the hair follicles.

At time T1, as cam 350 rotates such that extended radius portion 370 is no longer in contact with removal and suppression head 20, springs 380 cause removal and suppression head 20 to advance towards cam 350, specifically towards shortened radius portion 360 of cam 350. Removal and suppression head 20 is thus translated from the treatment position to a cooling position, also known as the second position, distance h(t) thereby increasing. In one embodiment, the distance between the treatment and cooling position of removal and suppression head 20 is between 2-20 mm and in one particular embodiment is 5 mm. In one embodiment, while removal and suppression head 20 is in the cooling position, control circuitry 70 is arranged to control current driver 120 to cease current flow through cutting element 110, thereby allowing cutting element 110 to cool. In one embodiment, control circuitry 70 is arranged to control current driver 60 to cease current flow through irradiating element 40, thereby allowing irradiating element 40 to cool.

At time T2, cam 350 completes a rotation and extended radius portion 370 again comes in contact with removal and suppression head 20, removal and suppression head 20 is advanced towards opening 17 of housing 15. Removal and suppression head 20 is thus translated to the treatment position, thereby raising the temperature of the epidermis of portion 130 of skin surface 140, as described above. In the embodiment where current flow through cutting element 110 is ceased while in the cooling position, control circuitry 70 is arranged to control current driver 120 to resume current flow through cutting element 110 at time T2. In the embodiment where current flow through irradiating element 40 is ceased while in the cooling position, control circuitry 70 is arranged to control current driver 60 to resume current flow through irradiating element 40 at time T2. At time T3, when extended radius portion 370 of cam 350 is no longer in contact with removal and suppression head 20, removal and suppression head 20 is again translated to the cooling position. As shown in curve 400, the temperature of the epidermis at time T3 is at a higher temperature than at time T1. At time T4, cam 350 completes a second rotation and extended radius portion 370 again comes in contact with removal and suppression head 20, removal and suppression head 20 again being translated to the treatment position as described above in relation to time T2. At time T5, extended radius portion 370 is no longer in contact with removal and suppression head 20, and removal and suppression head 20 is again translated to the cooling position, thereby repeating the process as described above in relation to time T3.

Advantageously, epidermis is heated to a high enough temperature to provide a thermal stimuli to a depth of 0.5 to about 1 mm below thereby suppressing hair growth, while the overall temperature rise of the outer portion of the epidermis is not significant enough to cause any damage to the epidermis. Additionally, the end of hair 150 in contact with cutting element 110 is further cut by the repeated heating action of cutting element 110.

In one embodiment, the time between each subsequent periodic translation of removal and suppression head 20 into the treatment position is between 0.5-500 ms, in one particular embodiment the periodicity being about 200 ms. Specifically, in one embodiment, the rotation frequency of cam 350 is between 2-2000 Hz, in one particular embodiment the frequency being about 5 Hz. In one embodiment, the duty cycle of the treatment position of removal and suppression head 20 is greater than 50%, i.e. the amount of time removal and suppression head 20 remains in the treatment position is greater than the amount of time removal and suppression head 20 remains in the cooling position. Specifically, the circumference of extended radius portion 370 of cam 350 is greater than the circumference of shortened radius portion 360. In one embodiment, the duty cycle of the treatment position of removal and suppression head 20 is about 60%. In one preferred embodiment, the duty cycle of the treatment position of removal and suppression head 20 and the rotation frequency of cam 350 are arranged such that portion 130 of skin surface 140 is not damaged from excess heat.

In one non-limiting embodiment, the above operation is responsive to an output of motion sensor 80 indicative that removal and suppression head 20 is in motion, particularly in relative motion in relation to skin surface 140, with a rate of relative motion greater than a predetermined minimum. In the event that motion sensor 80 detects that the rate of relative motion of housing 15 is below a predetermined limit, control circuitry 70 controls driver 60 and driver 120 to cease current flow through irradiating element 40 and cutting element 110, respectively. In one embodiment, control circuitry 70 is further arranged to cease rotation of cam 350 at a point where the rotation of cam 350 brings shortened radius portion 360 in contact with removal and suppression head 20 thus ensuring that removal and suppression head 20 is in the cooling position. Preferably, rotation of cam 350 and current flow through irradiating element 40 and cutting element 110 are ceased only in the event that motion sensor 80 detects that the rate of relative motion of housing 15 is below a predetermined limit, i.e. a safety threshold, for more than a predetermined time period. In one particular embodiment the predetermined limit is just above zero, and thus shut off occurs only when no relative motion is detected.

In one non-limiting embodiment, the treatment duty cycle is a function of the detected rate of relative motion of housing 15. Thus, irradiating element 40 is powered to provide irradiation for only a portion of the time that removal and suppression head 20 is in the treatment position. The treatment duty cycle is understood herein to mean the percentage of total cycle time of removal and suppression head 20 where irradiating element 40 is powered to provide heat. As the rate of relative motion of housing 15 increases, the treatment duty cycle increases and as the rate of relative motion of housing 15 decreases, the treatment duty cycle decreases.

In one embodiment, the duty cycle of removal and suppression head 20 is adjusted such that the amount of time removal and suppression head 20 is in the treatment position during each cycle of cam 350 is:

$$T=Y/V \qquad \text{EQ. 2}$$

where Y is the width of opening 26 of removal and suppression head 20 and V is the detected rate of relative motion of housing 15. Specifically, in one particular embodiment, in order to adjust the duty cycle of removal and suppression head 20, the rotational speed of cam 350 is separately adjusted during the period when shortened radius portion 360 is in contact with removal and suppression head 20 and during the period when extended radius portion 370 is in contact with removal and suppression head 20.

Figure 3A:
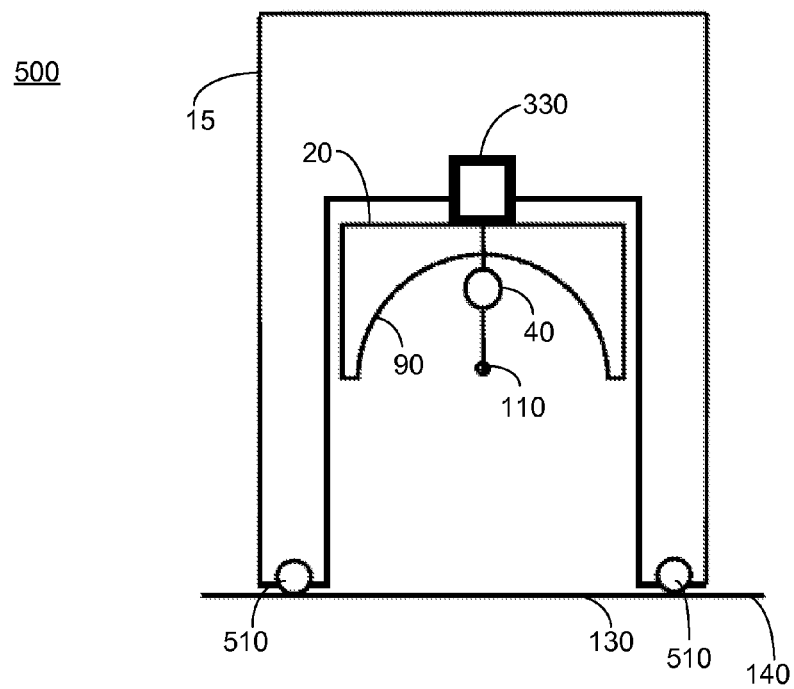
FIGS. 3A-3D illustrate various high level side cut views of a hair removal and re-growth suppression apparatus comprising a translating reflector, according to certain embodiments.
Figure 3B:
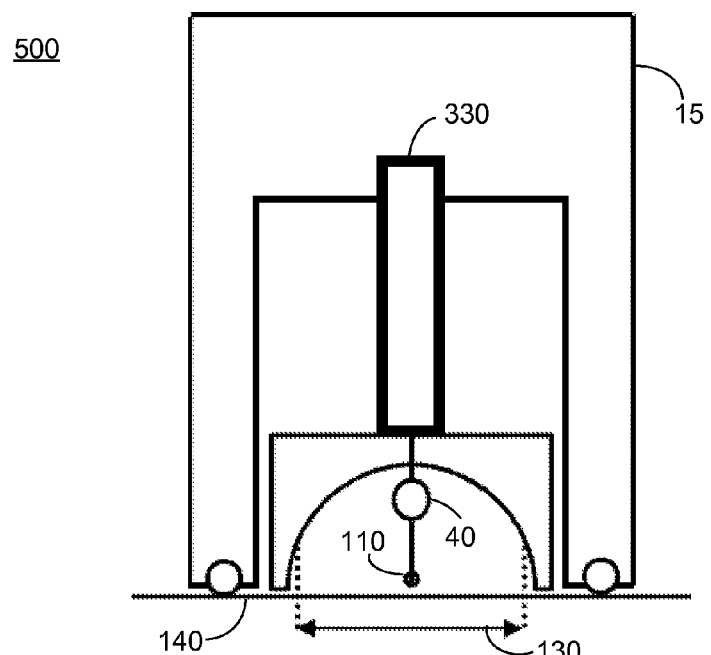
Figure 3C:
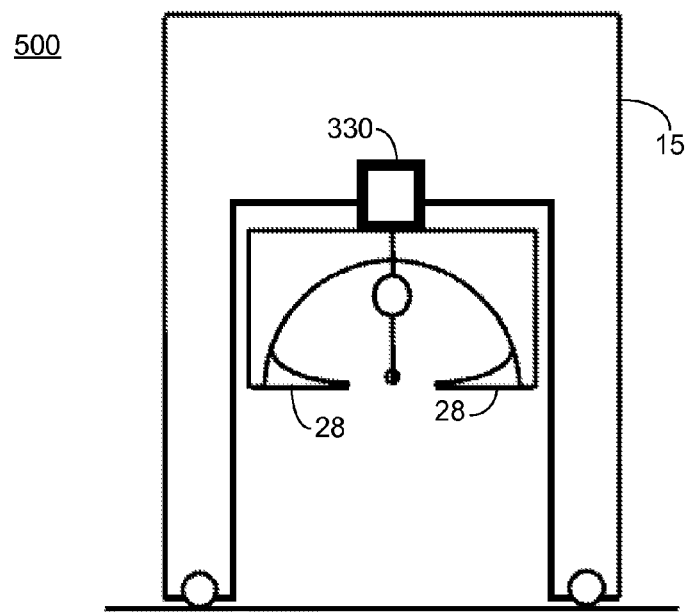
Figure 3D:
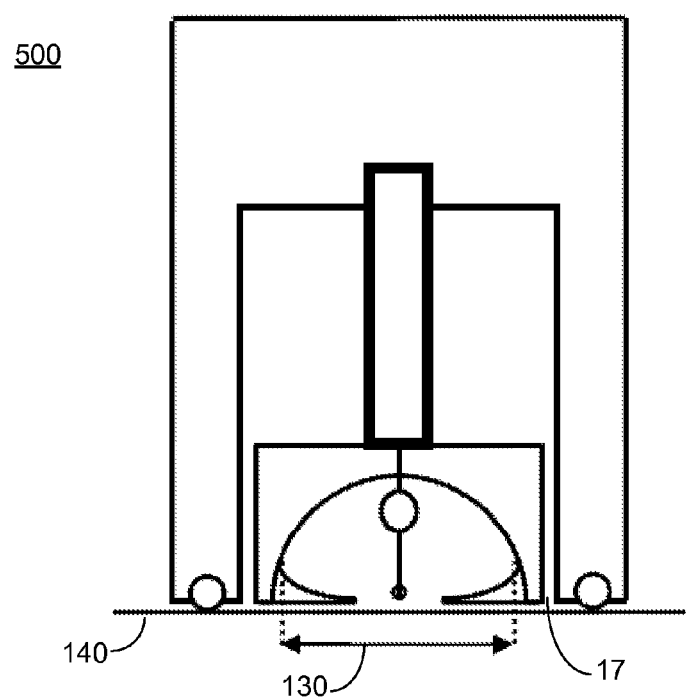

FIG. 3A illustrates a high level side cut view of a hair removal and re-growth suppression apparatus 500 with a removal and suppression head 20 in a cooling position; FIG. 3B illustrates a high level side cut view of hair removal and re-growth suppression apparatus 500 with removal and suppression head 20 in a treatment position; FIG. 3C illustrates a high level side cut view of hair removal and re-growth suppression apparatus 500 with a removal and suppression head 20 in a cooling position and further illustrating the teeth of longitudinal end 28 of extender assembly 23; and FIG. 3D illustrates a high level side cut view of hair removal and re-growth suppression apparatus 500 with removal and suppression head 20 in a treatment position and further illustrating the teeth of longitudinal end 28 of extender assembly 23. Hair removal and re-growth suppression apparatus 500 is in all respects similar to hair removal and re-growth suppression apparatus 300 of FIG. 2A, with the addition of rollers 510 attached to housing 15 and arranged to be in contact with skin surface 140 when opening 17 of housing 15 is juxtaposed therewith. For the sake of simplicity, the details of translation mechanism 330 are not illustrated. As described above in relation FIGS. 2A-2B, removal and suppression head 20 is regularly translated between a treatment position, as illustrated in FIGS. 3A and 3C, and a cooling position, as illustrated in FIGS. 3B and 3D. The operation of hair removal and re-growth suppression apparatus 500 is in all respects similar to hair removal and re-growth suppression apparatus 300 of FIG. 3A. Advantageously, rollers 510 and the teeth of longitudinal ends 28 of extender assembly 23 allow for smoother movement across skin surface 140. Additionally, the teeth of extender assembly 23 provides contact of a reduced surface area of extender assembly 23 with skin surface 140, thereby less heat is transferred from extender assembly 23 to skin surface 140. In the embodiment of FIGS. 3A-3D translation of irradiating element 40 is linked to translation of cutting element 110, however this is not meant to be limiting in any way. Independent translation mechanisms for each of irradiating element 40 and cutting element 110 may be provided without exceeding the scope.

Figure 4A:
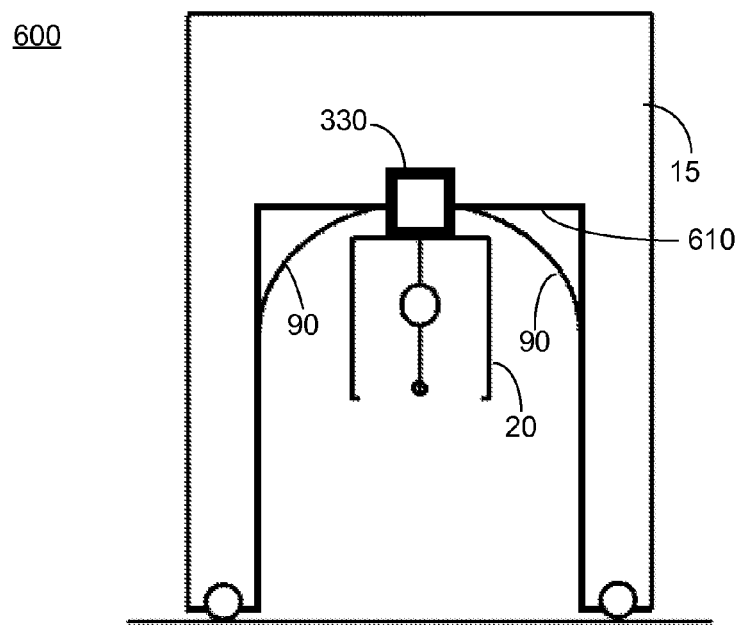
FIGS. 4A-4B illustrate various high level side cut views of a hair removal and re-growth suppression apparatus with a fixed reflector, according to certain embodiments.
Figure 4B:
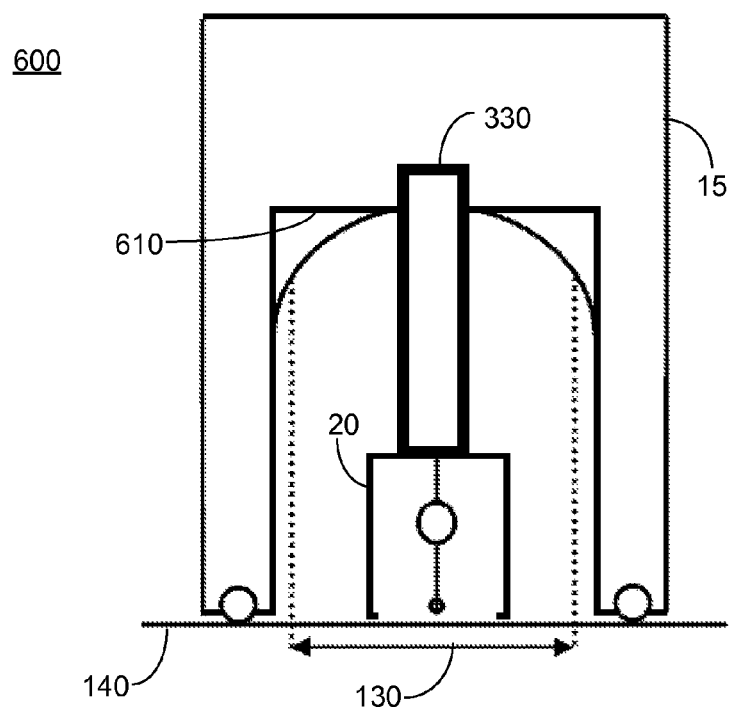

FIG. 4A illustrates a high level side cut view of a hair removal and re-growth suppression apparatus 600 with a removal and suppression head 20 in a cooling position and FIG. 4B illustrates a high level side cut view of hair removal and re-growth suppression apparatus 600 with removal and suppression head 20 in a treatment position. Hair removal and re-growth suppression apparatus 600 is in all respects similar to hair removal and re-growth suppression apparatus 500 of FIGS. 3A-3D, with the exception that reflector 90 is disposed on housing 15 instead of being disposed on removal and suppression head 20. Specifically, reflector 90 is disposed on a wall 610 of housing 15 facing opening 17. In one non-limiting embodiment, reflector 90 is spit in two, with translation mechanism 330 positioned between the two halves. As described above, removal and suppression head 20 is regularly translated between a treatment position, as illustrated in FIG. 4A, and a cooling position, as illustrated in FIG. 4B. Regardless of the position of removal and suppression head 20, reflector 90 remains in a fixed position in relation to housing 15.

Figure 5A:
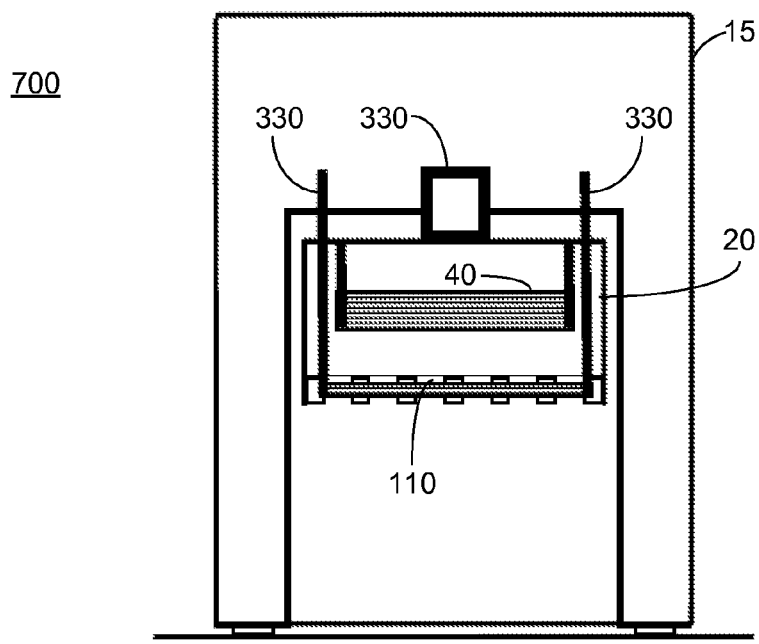
FIGS. 5A-5B illustrate various high level side cut views of a hair removal and re-growth suppression apparatus comprising an irradiating element and a cutting element and further comprising a separate translation mechanism for each element, according to certain embodiments.
Figure 5B:
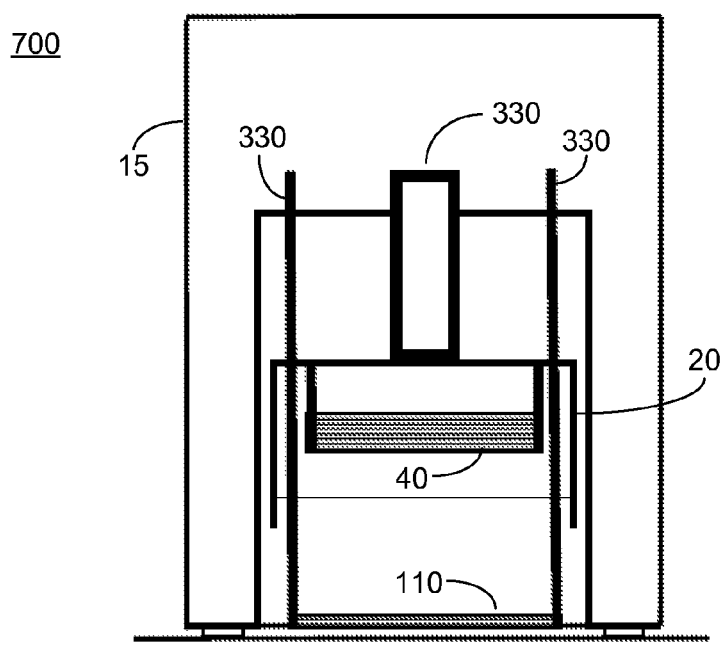

FIG. 5A illustrates a high level side cut view of a hair removal and re-growth suppression apparatus 700 with a removal and suppression head 20 in a cooling position and FIG. 5B illustrates a high level side cut view of hair removal and re-growth suppression apparatus 700 with removal and suppression head 20 in a treatment position. Hair removal and re-growth suppression apparatus 700 is in all respects similar to hair removal and re-growth suppression apparatus 500 of FIGS. 3A-3B, with the exception that separate translation mechanisms 330 are provided for each of irradiating element 40 and cutting element 110. The operation of hair removal and re-growth suppression apparatus 700 is in all respects similar to the operation of hair removal and re-growth suppression apparatus 500, with the exception that cutting element 110 is translated independent of the translation of removal and suppression head 20. In one embodiment, when removal and suppression head 20 is in the treatment position, cutting element 110 is further translated towards portion 130 of skin surface 140 such that the distance between cutting element 110 and skin surface 140 is less than the distance between irradiation element 40 and skin surface 140. In one embodiment, cutting element 110 is maintained at a distance of less than 3 mm from portion 130 of skin surface 140 regardless of the position of removal and suppression head 20. In the event motion sensor 80 detects that the relative motion of housing 15 is less than a predetermined value, control circuitry 70 is arranged to control the respective translation mechanism 330 to translate cutting element 110 away from skin surface 140 to a cooling position as described above.

Figure 6:
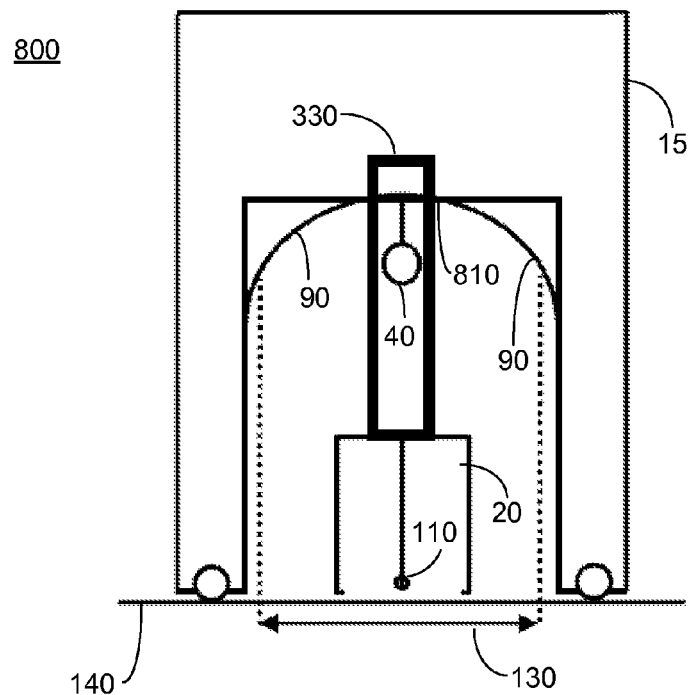
FIG. 6 illustrates a high level side cut view of a hair removal and re-growth suppression apparatus comprising a fixed irradiating element, a cutting element and a translation mechanism arranged to translate the cutting element between a first and a second position, according to certain embodiments.

FIG. 6 illustrates a high level side cut view of a hair removal and re-growth suppression apparatus 800, with a removal and suppression head 20 in a treatment position. Hair removal and re-growth suppression apparatus 800 is in all respects similar to hair removal and re-growth suppression apparatus 600 of FIGS. 4A-4B, with the exception that irradiating element 40 is fixed in relation to a wall 810 of housing 15. As described above, removal and suppression head 20 is regularly translated between a treatment position and a cooling position. Regardless of the position of removal and suppression head 20, irradiating element 40 and reflector 90 remain fixed in relation to housing 15. In one embodiment, regardless of the position of removal and suppression head 20, control circuitry 70 is arranged to control driver 60 to maintain current flow through irradiating element 40, thereby portion 130 of skin surface 140 is constantly irradiated.

Figure 7A:
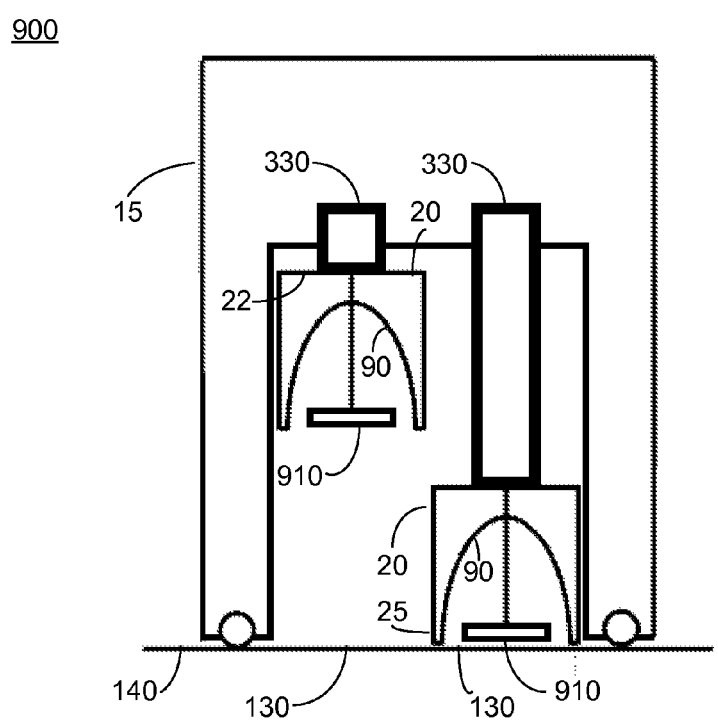
FIGS. 7A-7B illustrate various high level side cut views of a hair removal and re-growth suppression apparatus comprising a plurality of irradiating and cutting elements and a plurality of translation mechanisms.
Figure 7B:
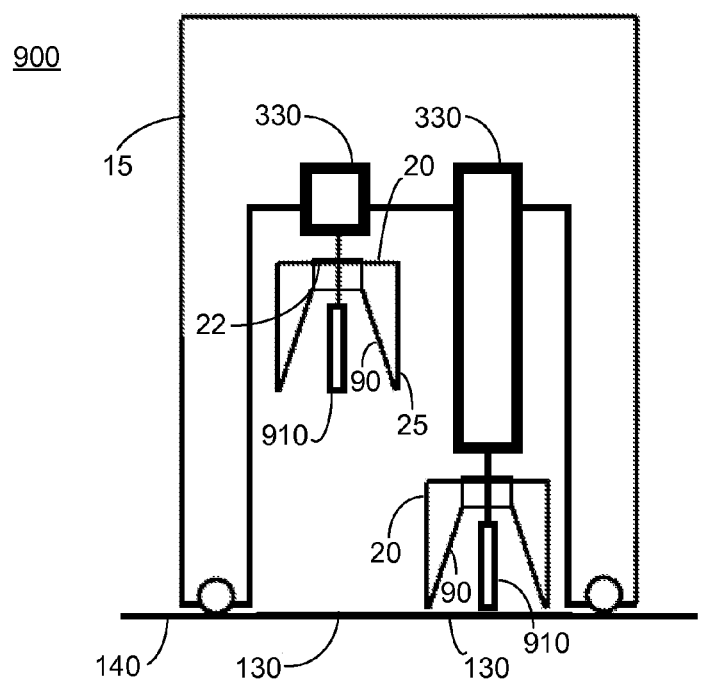

FIGS. 7A-7B illustrate high level side cut views of a hair removal and re-growth suppression apparatus 900, the figures being described together. Hair removal and re-growth suppression apparatus 900 is in all respects similar to hair removal and re-growth suppression apparatus 500 of FIGS. 3A-3B, with the exception that: a pair of removal and suppression heads 20 are provided; and irradiating element 40 and cutting element 110 are replaced with an irradiating and cutting element 910. A translation mechanism 330 is provided for each removal and suppression head 20 and, in one embodiment, arranged as described above in relation to FIG. 2A. In one embodiment (not shown), a driver 60 is provided for each irradiating and cutting element 910 and is arranged to drive current therethrough. In another embodiment, only a single driver 60 is provided and is arranged to drive current through each irradiating and cutting element 910. In one embodiment, as illustrated in FIG. 7A, each reflector 90 is elongated concave shaped. In another embodiment, as illustrated in FIG. 7B, reflector 90 is an elongated open trapezoid shaped. In one particular embodiment, the open trapezoid shape is an isosceles trapezoid with the wide base open.

In one embodiment, irradiating and cutting element 910 comprises a Nickel Chromium alloy. In one further embodiment, irradiating and cutting element 910 comprises Nichrome. In another embodiment, irradiating and cutting element 910 comprises a Molybdenum disilicide alloy. In another embodiment, irradiating and cutting element 910 comprises a ferritic iron-chromium-aluminum alloy. In one embodiment, irradiating and cutting element 910 is arranged to output EMR exhibiting about 95% of its energy within a spectrum of between 500-5000 nm, in one particular embodiment the EMR exhibiting less than 10% of its energy within a spectrum of between 500-1000 nm. In one embodiment, the output EMR exhibits about 95% of its energy around a wavelength of 1000 nm. In one embodiment, irradiating and cutting element 910 is arranged to be heated up to a temperature of 400-1900° C. responsive to an appropriate current flowing therethrough. In one particular embodiment, irradiating and cutting element 910 is arranged to be heated up to a temperature of 1000°-1900° C. and in one further embodiment to a temperature of about 1900° C., responsive to an appropriate current flowing therethrough. In another embodiment, irradiating and cutting element 910 is arranged to be heated to a temperature greater than 1900° C.

In one embodiment, irradiating and cutting element 910 is elongated rectangular cuboid shaped. In one embodiment, as illustrated in FIG. 7A, the edge of irradiating and cutting element 910 facing wall 22 of removal and suppression head 20, and the edge parallel thereto, are wider than the edges parallel to parallel arms 25, as described above in relation to FIGS. 1A-1C. In another embodiment, as illustrated in FIG. 7B, the edge of irradiating and cutting element 910 facing wall 22 of removal and suppression head 20, and the edge parallel thereto, are narrower than the edges parallel to parallel arms 25. In one embodiment, the length of irradiating and cutting element 910 is 1-100 times longer than the width thereof. In one particular embodiment, the length of irradiating and cutting element 910 is 5 times longer than the width thereof. In another embodiment, the length of irradiating and cutting element 910 is more than 100 times longer than the width thereof. In another embodiment, irradiating and cutting element 910 is cylinder shaped. In another embodiment, irradiating and cutting element 910 is elongated square cuboid shaped.

In operation, as described above, each removal and suppression head 20 is regularly translated between a treatment position and a cooling position. In the treatment position, driver 60 is arranged to drive current through irradiating and cutting element 910, thereby irradiating portion 130 of skin surface 140 and cutting hairs protruding there from, as described above in relation to irradiating element 40 and cutting element 110. In one embodiment, in the cooling position, driver 60 is arranged to cease current flow through irradiating and cutting element 910. In one embodiment, removal and suppression heads 20 are alternately translated to the treatment position, with each removal and suppression head 20 being translated to the treatment position only when the other removal and suppression head 20 is in the cooling position. In another embodiment, the treatment time of both removal and suppression heads 20, i.e. the time period each removal and suppression head 20 is in the treatment position, at least partially overlaps. In one embodiment, the duty cycle of both removal and suppression heads 20, i.e. the percentage of time each removal and suppression head 20 is in the treatment position, are equal. In one embodiment, the duty cycle of each removal and suppression head 20 is about 60%. In another embodiment, the duty cycle of each removal and suppression head 20 is less than 50%. In one embodiment, the duty cycle of each removal and suppression head 20 is controlled responsive to the detected rate of relative motion of housing 15, as described above in relation to hair removal and re-growth suppression apparatus 300 of FIGS. 2A-2B. In one embodiment, the driving pulse time of each irradiating and cutting element 910, denoted TK, is:

$$TK = XK/V \qquad \text{EQ. 2}$$

where XK is the width of each irradiating and cutting element 910 and V is the detected rate of relative motion of housing 15. In one embodiment, the size of each irradiating and cutting element 910 and the positions of removal and suppression heads 20 are arranged such that a gap exits between both openings 26 of removal and suppression heads 20. Advantageously, portion 130 of skin surface 140 cools during the time the gap is juxtaposed therewith, i.e. during the time portion 130 is not exposed to either irradiating and cutting element 910. The above has been described in an embodiment where two removal and suppression heads 20 are provided, however this is not meant to be limiting in any way and any number of removal and suppression heads 20 can be provided without exceeding the scope.

Figure 8A:
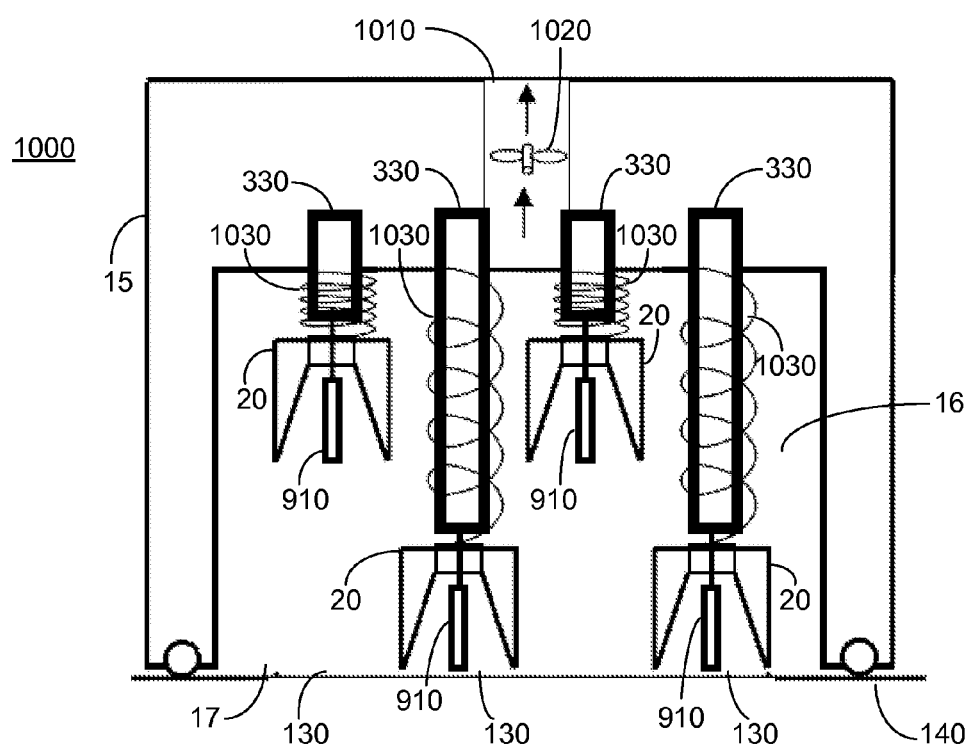
FIG. 8A illustrates a high level side cut view of a hair removal and re-growth suppression apparatus comprising a plurality of irradiating and cutting elements, a plurality of translation mechanisms and a heat vent.
Figure 8B:
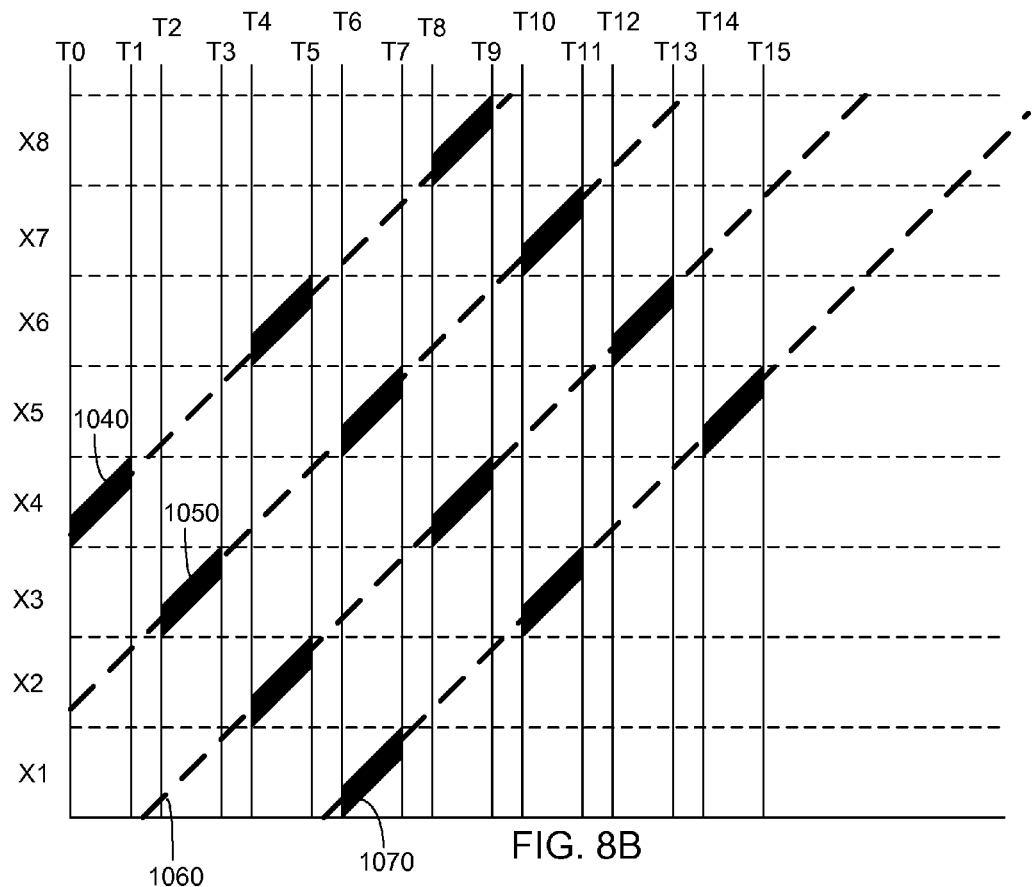
FIG. 8B illustrates a graph describing the operation of the hair removal and re-growth suppression apparatus of FIG. 8A.

FIG. 8A illustrates a high level side cut view of a hair removal and re-growth suppression apparatus 1000 and FIG. 8B illustrates a graph describing the operation of hair removal and re-growth suppression apparatus 1000, where the x-axis represents time in arbitrary units and the y-axis represents skin area in arbitrary units, the figures being described together. Hair removal and re-growth suppression apparatus 1000 is in all respects similar to hair removal and re-growth suppression apparatus 900 of FIGS. 7A-7B, with the exception that: four removal and suppression heads 20 are provided; a heat vent 1010, comprising a fan 1020, is provided; and a plurality of springs 1030 are provided. Heat vent 1010 extends from cavity 16 of housing 15 to the ambient air external of housing 15. Fan 1020 is situated within heat vent 1010. A first end of each spring 1030 is connected to housing 15 and a second end of each spring 1030 is connected to a particular removal and suppression head 20. The operation of hair removal and re-growth suppression apparatus 1000 is in all respects similar to the operation of hair removal and re-growth suppression apparatus 900 of FIGS. 7A-7B. Advantageously, heat vent 1010 is arranged to vent excess heat away from skin surface 140. In one embodiment, fan 1020 is arranged to be in continuous operation so as to aid in the venting of heat. In one embodiment, as illustrated in the graph of FIG. 8B, removal and suppression heads 20 are arranged and operated such that each portion 130 of skin surface 140 is irradiated by two removal and suppression heads 20.

Plot 1040 illustrates the area of skin surface 140 irradiated by a first removal and suppression head 20, wherein a dashed line indicates that first removal and suppression head 20 is not energized and a solid line indicates that first removal and suppression head 20 is energized. Plot 1050 illustrates the area of skin surface 140 irradiated by a second removal and suppression head 20, wherein a dashed line indicates that first removal and suppression head 20 is not energized and a solid line indicates that first removal and suppression head 20 is energized. Plot 1060 illustrates the area of skin surface 140 irradiated by a third removal and suppression head 20, wherein a dashed line indicates that first removal and suppression head 20 is not energized and a solid line indicates that first removal and suppression head 20 is energized. Plot 1070 illustrates the area of skin surface 140 irradiated by a fourth removal and suppression head 20, wherein a dashed line indicates that first removal and suppression head 20 is not energized and a solid line indicates that first removal and suppression head 20 is energized.

At time T0, first and third removal and suppression heads 20 are translated to the treatment position, as described above, and a portion 130 of skin surface 140, denoted X4, is irradiated by irradiating and cutting element 910 of first removal and suppression head 20 until time T1. The portion of skin surface 140 irradiated by irradiating and cutting element 910 of third removal and suppression head 20 during the period from T1 to T2 is not illustrated in FIG. 8B. Areas X1-X3 of skin surface 140 are not irradiated and are therefore allowed to cool. At time T1, first and third removal and suppression heads 20 are translated to the cooling position and area X4 begins to cool. At time T2, second and fourth removal and suppression heads 20 are translated to the treatment position, as described above and a portion 130 of skin surface 140, denoted X3, is irradiated by irradiating and cutting element 910 of second removal and suppression head 20 until time T3. The portion of skin surface 140 irradiated by irradiating and cutting element 910 of fourth removal and suppression head 20 during the period from T2 to T3 is not illustrated in FIG. 8B. Areas X1, X2 and X4 are not irradiated and are therefore allowed to cool. At time T3, second and fourth removal and suppression heads 20 are translated to the cooling position and area X3 begins to cool.

At time T4, first and third removal and suppression heads 20 are translated to the treatment position. A portion 130 of skin surface 140, denoted X6, is irradiated by irradiating and cutting element 910 of first removal and suppression head 20 and a portion 130 of skin surface 140, denoted X2, is irradiated by irradiating and cutting element 910 of third removal and suppression head 20 until time T5. At time T5, first and third removal and suppression heads 20 are translated to the cooling position and areas X2 and X6 begin to cool. At time T6, second and fourth removal and suppression heads 20 are translated to the treatment position. A portion 130 of skin surface 140, denoted X5, is irradiated by irradiating and cutting element 910 of second removal and suppression head 20 and a portion 130 of skin surface 140, denoted X1, is irradiated by irradiating and cutting element 910 of fourth removal and suppression head 20 until time T7. At time T7, second and fourth removal and suppression heads 20 are translated to the cooling position and areas X1 and X5 begin to cool.

At time T8, first and third removal and suppression heads 20 are translated to the treatment position. A portion 130 of skin surface 140, denoted X8, is irradiated by irradiating and cutting element 910 of first removal and suppression head 20 and portion X4 of skin surface 140 is irradiated by irradiating and cutting element 910 of third removal and suppression head 20 until time T9. As described above, portion X4 was irradiated during the time interval between T0 and T1. Thus, treatment is again provided to portion X4. At time T9, first and third removal and suppression heads 20 are translated to the cooling position and areas X4 and X8 begin to cool. At time T10, second and fourth removal and suppression heads 20 are translated to the treatment position. A portion 130 of skin surface 140, denoted X7, is irradiated by irradiating and cutting element 910 of second removal and suppression head 20 and portion X3 of skin surface 140 is irradiated by irradiating and cutting element 910 of fourth removal and suppression head 20 until time T11. As described above, portion X3 was irradiated during the time interval between T2 and T3. Thus, treatment is again provided to portion X3. At time T11, second and fourth removal and suppression heads 20 are translated to the cooling position and areas X3 and X7 begin to cool.

At time T12, first and third removal and suppression heads 20 are translated to the treatment position. Portion X6 of skin surface 140 is irradiated by irradiating and cutting element 910 of third removal and suppression head 20 until time T13. As described above, portion X6 was irradiated during the time interval between T4 and T5. Thus, treatment is again provided to portion X6. The portion 130 of skin surface 140 irradiated by irradiating and cutting element 910 of first removal and suppression head 20 during the time interval between T12 and T13 is not illustrated. At time T13, first and third removal and suppression heads 20 are translated to the cooling position and area X6 begins to cool. At time T14, second and fourth removal and suppression heads 20 are translated to the treatment position. Portion X5 of skin surface 140 is irradiated by irradiating and cutting element 910 of fourth removal and suppression head 20 until time T15. As described above, portion X5 was irradiated during the time interval between T6 and T7. Thus, treatment is again provided to portion X5. The portion 130 of skin surface 140 irradiated by irradiating and cutting element 910 of second removal and suppression head 20 during the time interval between T14 and T15 is not illustrated. At time T15, second and fourth removal and suppression heads 20 are translated to the cooling position and area X5 begins to cool.

Advantageously, the arrangement and operation of hair removal and re-growth suppression apparatus 1000 provides for multiple treatment of skin surface 140, with each removal and suppression head 20 exhibiting a duty rate of less than 50%. In one embodiment, each spring 1030 is arranged to translate the respective removal and suppression head 20 from the treatment position to the cooling position in the event of malfunction of the respective translation mechanism 330.

Figure 9:
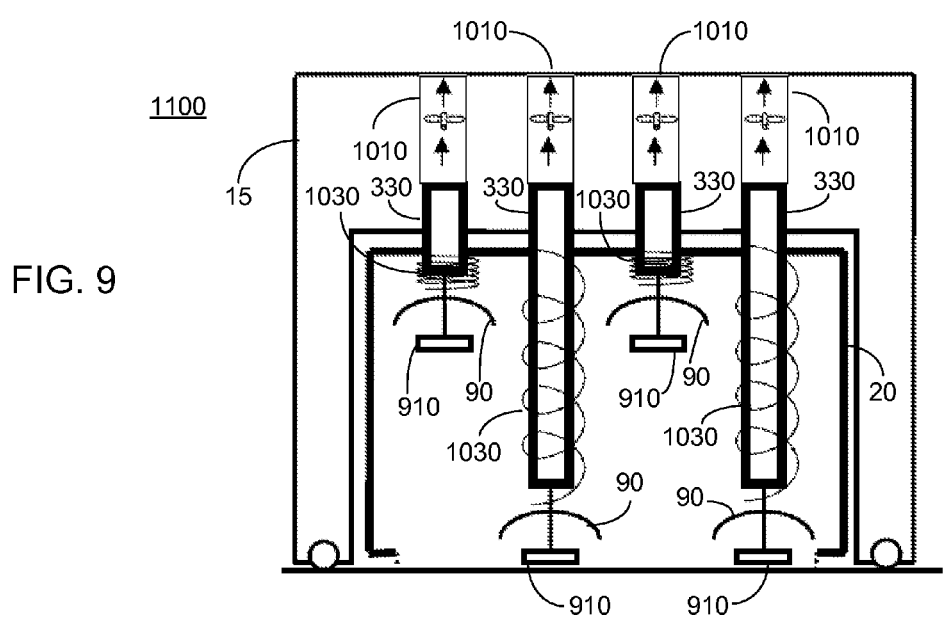
FIG. 9 illustrates a high level side cut view of a hair removal and re-growth suppression apparatus comprising a plurality of irradiating and cutting elements, a plurality of translation mechanisms and a single removal and suppression head.

FIG. 9 illustrates a high level side cut view of a hair removal and re-growth suppression apparatus 1100. Hair removal and re-growth suppression apparatus 1100 is in all respects similar to hair removal and re-growth suppression apparatus 1000 of FIG. 8A, with the exception that only a single removal and suppression head 20 is provided. Each irradiating and cutting element 910 and the reflector 90 associated therewith is connected to a respective translation mechanism 330. A first end of each spring 1030 is connected to a respective reflector 90 and a second end of each spring 1030 is connected to removal and suppression head 20. A plurality of heat vents 1010 are provided, each associated with a respective irradiating and cutting element 910.

Figure 10:
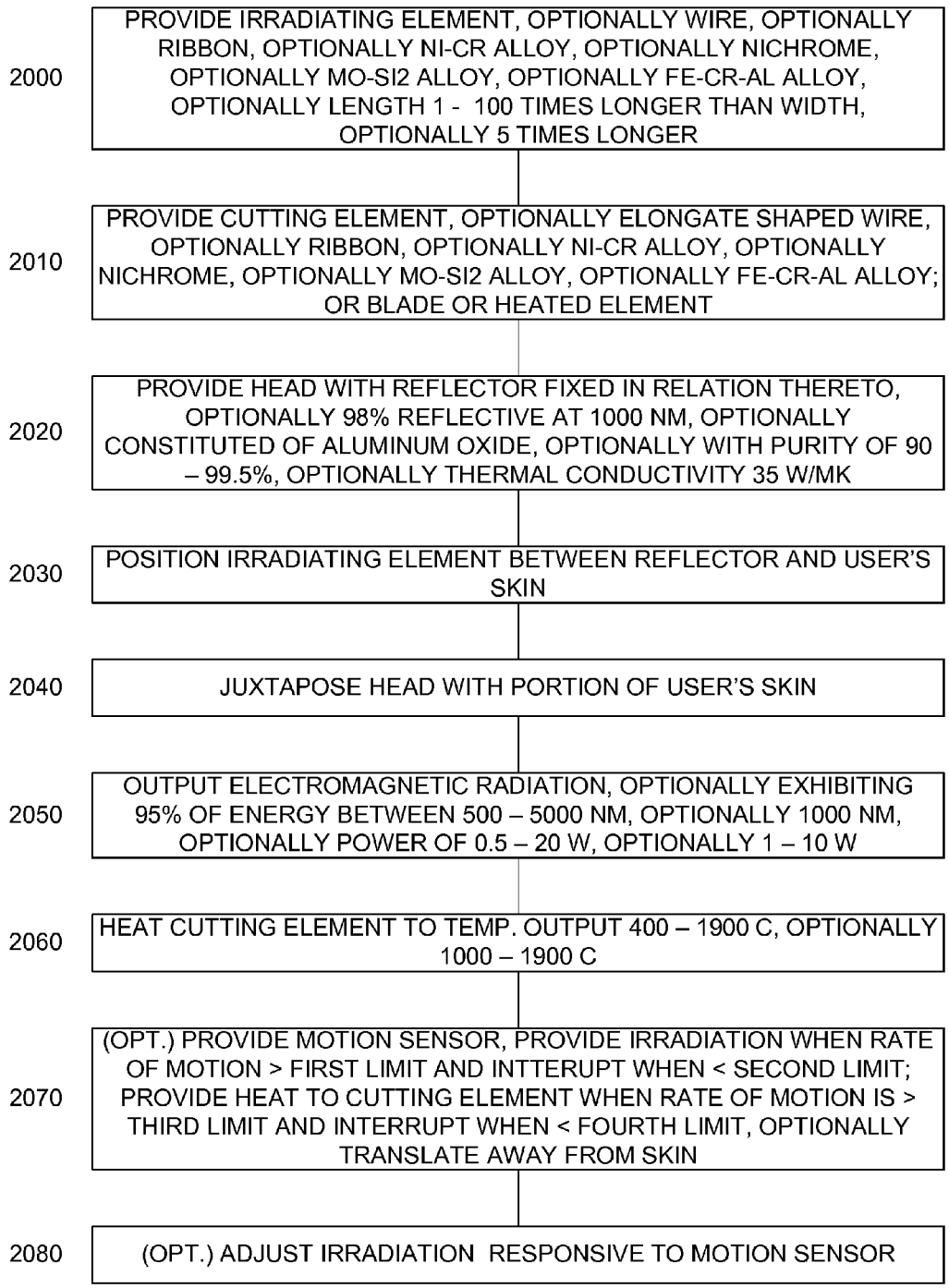
FIG. 10 illustrates a high level flow chart of a first method of operation of a hair removal and re-growth suppression apparatus comprising an irradiating element, a reflector and a cutting element, according to certain embodiments.

FIG. 10 illustrates a high level flow chart of a first method of operation of a hair removal and re-growth suppression apparatus comprising an irradiating element, a reflector and a cutting element, according to certain embodiments. In stage 2000, an irradiating element is provided. In one embodiment, the irradiating element comprises a wire. In another embodiment, the irradiating element comprises a ribbon. In one embodiment, the irradiating element comprises a Nickel Chromium alloy. In one further embodiment, the irradiating element comprises Nichrome. In another embodiment, the irradiating element comprises a Molybdenum disilicide alloy. In another embodiment, the irradiating element comprises a ferritic iron-chromium-aluminum alloy. In one embodiment, the irradiating element is arranged to output EMR exhibiting about 95% of its energy within a spectrum of between 500-5000 nm, in one particular embodiment the EMR exhibiting less than 10% of its energy within a spectrum of between 500-1000 nm. In one embodiment, the output EMR exhibits about 95% of its energy around a wavelength of 1000 nm. In one embodiment, the irradiating element is arranged to be heated to a temperature of 400°-1900° C. responsive to an appropriate current flowing therethrough, the EMR output responsive to heating of the irradiating element. In one particular embodiment, the irradiating element is arranged to be heated to a temperature of 1000°-1900° C. and in one further embodiment to a temperature of about 1900° C., responsive to an appropriate current flowing therethrough. In another embodiment, the irradiating element is arranged to be heated to a temperature greater than 1900° C.

In one embodiment, the irradiating element is elongated square cuboid shaped. In another embodiment, the irradiating element is elongated rectangular cuboid shaped. In another embodiment, the irradiating element is cylinder shaped. In one embodiment, the length of the irradiating element is 1-100 times longer than the width thereof. In one particular embodiment, the length of the irradiating element is 5 times longer than the width thereof. In another embodiment, the length of the irradiating element is more than 100 times longer than the width thereof.

In stage 2010, a cutting element is provided. In one embodiment, the cutting element comprises one of an elongate shaped wire, a ribbon, a blade and a heated element. In one embodiment, the cutting element comprises a Nickel Chromium alloy. In one further embodiment, the cutting element comprises Nichrome. In another embodiment, the cutting element comprises a Molybdenum disilicide alloy. In another embodiment, the cutting element comprises a ferritic iron-chromium-aluminum alloy.

In stage 2020, a removal and suppression head is provided, each of the provided irradiating element and cutting element of stages 2000 and 2010 secured in relation thereto, with a reflector disposed on the provided removal and suppression head. The term secured is not limited to a fixed connection and in one embodiment at least one of the provided irradiating element and provided cutting element is translatable in relation to the provided removal and suppression head as described above in relation to FIGS. 5A, 5B and 9. In one embodiment, the reflector is constituted of reflective material arranged to substantially reflect EMR exhibiting wavelengths between 500-5000 nm. In one embodiment, the reflector is constituted of Aluminum Oxide, in one further embodiment the purity being between 90-99.5%. In one embodiment, the reflectivity of the reflector is at least 96% at 500 nm and 98% at 1000 nm. In one embodiment, the thermal conductivity of the reflector is about 35 W/mK°. In stage 2030, the irradiating element of stage 2000 is positioned in front of the reflector of stage 2020, so that the irradiating element is positioned between the reflector and a skin surface, as will be described further below.

In stage 2040, the provided removal and suppression head of stage 2020 is juxtaposed with a portion of a skin surface. In stage 2050, the irradiating element outputs EMR, responsive to current flowing therethrough causing heating thereof. In one embodiment, as described above, the output EMR exhibits about 95% of its power within a spectrum between 500-5000 nm, in one particular embodiment the EMR exhibits less than 10% of its power within a spectrum between 500-1000 nm. In one embodiment, the output EMR exhibits about 95% of its energy around a wavelength of 1000 nm. In one embodiment the irradiating element is arranged to output EMR exhibiting a power between 0.5-20 W, in one particular embodiment with a power between 1-10 W. In one embodiment, the output EMR exhibits a fluence, measured at the portion of the skin surface juxtaposed with the removal and suppression head of stage 2020, of between 0.5-10 J/cm², in one particular embodiment the fluence being about 3 J/cm². The EMR output by the irradiating element is reflected off the reflector towards the portion of the skin surface which is juxtaposed with the indent of the head. Advantageously, heat output by the irradiating element is not substantially reflected off the reflector towards the skin surface.

In stage 2060, the cutting element of stage 2010 is heated to a temperature sufficient to cut hair. In one embodiment, the cutting element is heated to a temperature of 400°-1900° C., in one particular embodiment, to a temperature of 1000°-1900° C.

In optional stage 2070, a motion sensor is provided. In one embodiment, the motion sensor is arranged to output a signal responsive to the relative motion of the housing of stage 2020 in relation to a juxtaposed skin surface. In one embodiment, in the event that relative motion detected by the motion sensor is greater than a first predetermined value, irradiation by the provided irradiating element of stage 2000 is provided, and in the event that relative motion detected by the motion sensor is less than a second predetermined value, irradiation is interrupted. In one embodiment, the first predetermined value and the second predetermined value are the same. In the event that relative motion detected by the motion sensor is greater than a third predetermined value, the cutting element of stage 2010 is heated to a temperature sufficient to cut hair, and further optionally moved into a hair cutting position. In the event that relative motion detected by the motion sensor is less than a fourth predetermined value, power to the cutting element is interrupted, and further optionally moved into a non-cutting position. In one embodiment, the third predetermined value and the fourth predetermined value are the same. In one embodiment, the first predetermined value is less than the third predetermined value.

In optional stage 2080, power through the irradiating element of stage 2000 and the cutting element of stage 2010 is controlled responsive to the motion sensor. In one embodiment, the duty cycle is increased as the rate of relative motion of the removal and suppression head of stage 2020 increases and the duty cycle is decreased as the rate of relative motion of the removal and suppression head decreases. In one embodiment, current flowing through the irradiating element and the cutting element is increased as the rate of relative motion of the removal and suppression head increases and is decreased as the rate of relative motion of the removal and suppression head decreases.

The above has been described in an embodiment wherein the cutting element is an elongated heated element, however this is not meant to be limiting in any way. In another embodiment the cutting element is a blade.

Figure 11:
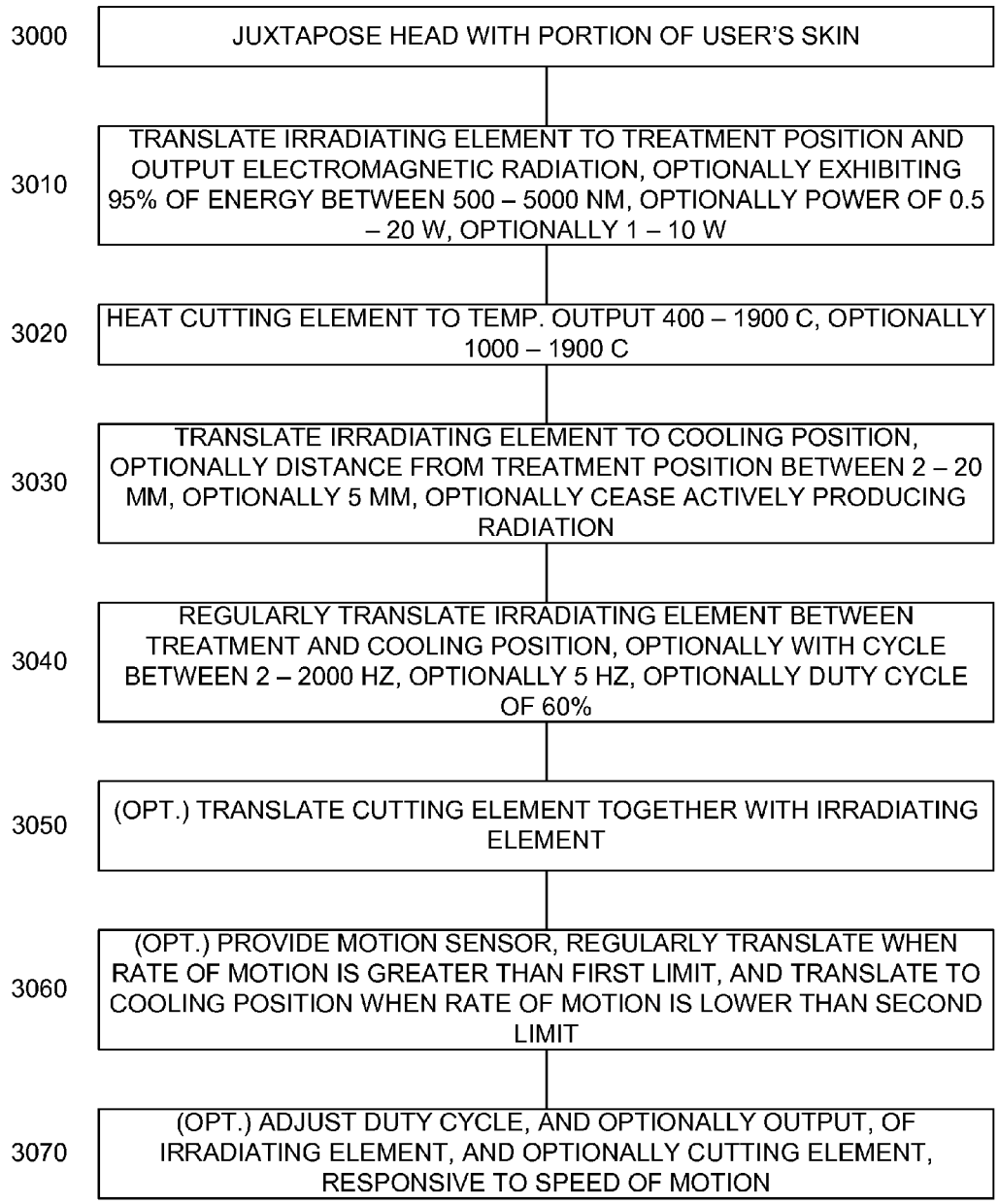
FIG. 11 illustrates a high level flow chart of a second method of operation of the hair removal and re-growth suppression apparatus, incorporating certain stages of FIG. 10.

FIG. 11 illustrates a high level flow chart of a second method of operation of the hair removal and re-growth suppression apparatus after stages 2000-2030 of FIG. 10, according to certain embodiments. In stage 3000, as described in stage 2040 of FIG. 10, the removal and suppression head of stage 2020 is juxtaposed with a portion of a skin surface. In stage 3010, the irradiating element of stage 2000 is translated to a treatment position. As described above, the irradiating element outputs EMR responsive to current flowing therethrough causing heating thereof. In one embodiment, the output EMR exhibits about 95% of its power within a spectrum between 500-5000 nm, in one particular embodiment the EMR exhibiting less than 10% of its power within a spectrum of 500-1000 nm. In one embodiment, the output EMR exhibits about 95% of its energy around a wavelength of 1000 nm. In one embodiment, the irradiating element outputs EMR with a power of 0.5-20 W, in one particular embodiment with a power of 1-10 W. In one embodiment, the output EMR exhibits a fluence, measured at the portion of the skin surface juxtaposed with the removal and suppression head of stage 2020, of 0.5-10 J/cm$^2$, in one particular embodiment the fluence being about 3 J/cm$^2$. The EMR output by the irradiating element is reflected off the reflector of stage 2020 towards the portion of the skin surface which is juxtaposed with the indent of the removal and suppression head. Advantageously, heat is not substantially reflected off the reflector towards the skin surface.

In stage 3020, the cutting element of stage 2010 is heated to a temperature sufficient to cut hair. In one embodiment, the cutting element is heated to a temperature of 400°-1900° C. In one particular embodiment, the cutting element is heated to a temperature of 1000°-1900° C. In one embodiment, the distance between the cutting element and the skin surface in the treatment position is less than 3 mm, and in one particular embodiment is 0.1-1 mm. In another embodiment, the cutting element is in contact with the skin.

In stage 3030, the irradiating element is translated from the treatment position of stage 3010 to a cooling position. In one embodiment, the distance between the treatment position and the cooling position is 2-20 mm and in one particular embodiment is about 5 mm. In one embodiment, the irradiating element is arranged to cease actively producing heat, and thus cease actively producing EMR, when translated to the cooling position. In stage 3040, the irradiating element is regularly translated between the treatment position of stage 3010 and the cooling position of stage 3030. In one embodiment, the cycle of the irradiating element between subsequent translations to the treatment position is 2-2000 Hz, preferably about 5 Hz. In one embodiment, the duty cycle of the irradiating element, i.e. the percentage of time the irradiating element is in the treatment position is about 60%. In optional stage 3050, the cutting element of stage 2010 is translated together with the irradiating element of stage 2000 between the treatment and cooling position. In one embodiment, in the cooling position, the cutting element ceases to actively produce heat.

In optional stage 3060, a motion sensor is provided. In one embodiment, the motion sensor is arranged to output a signal responsive to the relative motion of the removal and suppression head of stage 2020. In one embodiment, in the event that the rate of relative motion detected by the motion sensor is greater than a first predetermined value, regular translation of the irradiating element between the treatment position of stage 3010 and the cooling position of stage 3030 is provided, and in the event that relative motion detected by the motion sensor is less than a second predetermined value, the regular translation is interrupted. In one embodiment, heat production, and thus electromagnetic production, by the irradiating element of stage 2000 is interrupted. In one embodiment, the irradiating element is translated to the cooling position. In one further embodiment, the cutting element of stage 2010 is also translated to the cooling position and ceases to actively produce heat. In one embodiment, the first predetermined value and the second predetermined value are equal.

In optional stage 3070, the duty cycle of the irradiating element of stage 3040 is controlled responsive to the provided motion sensor of stage 3060. In one embodiment, the duty cycle is increased as the rate of relative motion of the removal and suppression head of stage 2020 increases and the duty cycle is decreased as the rate of relative motion of the removal and suppression head decreases. Further optionally, the output of the irradiating element is controlled responsive to the provided motion sensor. In one embodiment, current flowing through the irradiating element is increased as the rate of relative motion of the removal and suppression head increases and is decreased as the rate of relative motion of the removal and suppression head decreases. Optionally, current flowing through the cutting element of stage 2010 is increased as the rate of relative motion of the removal and suppression head increases and is decreased as the rate of relative motion of the removal and suppression head decreases.

Figure 12:
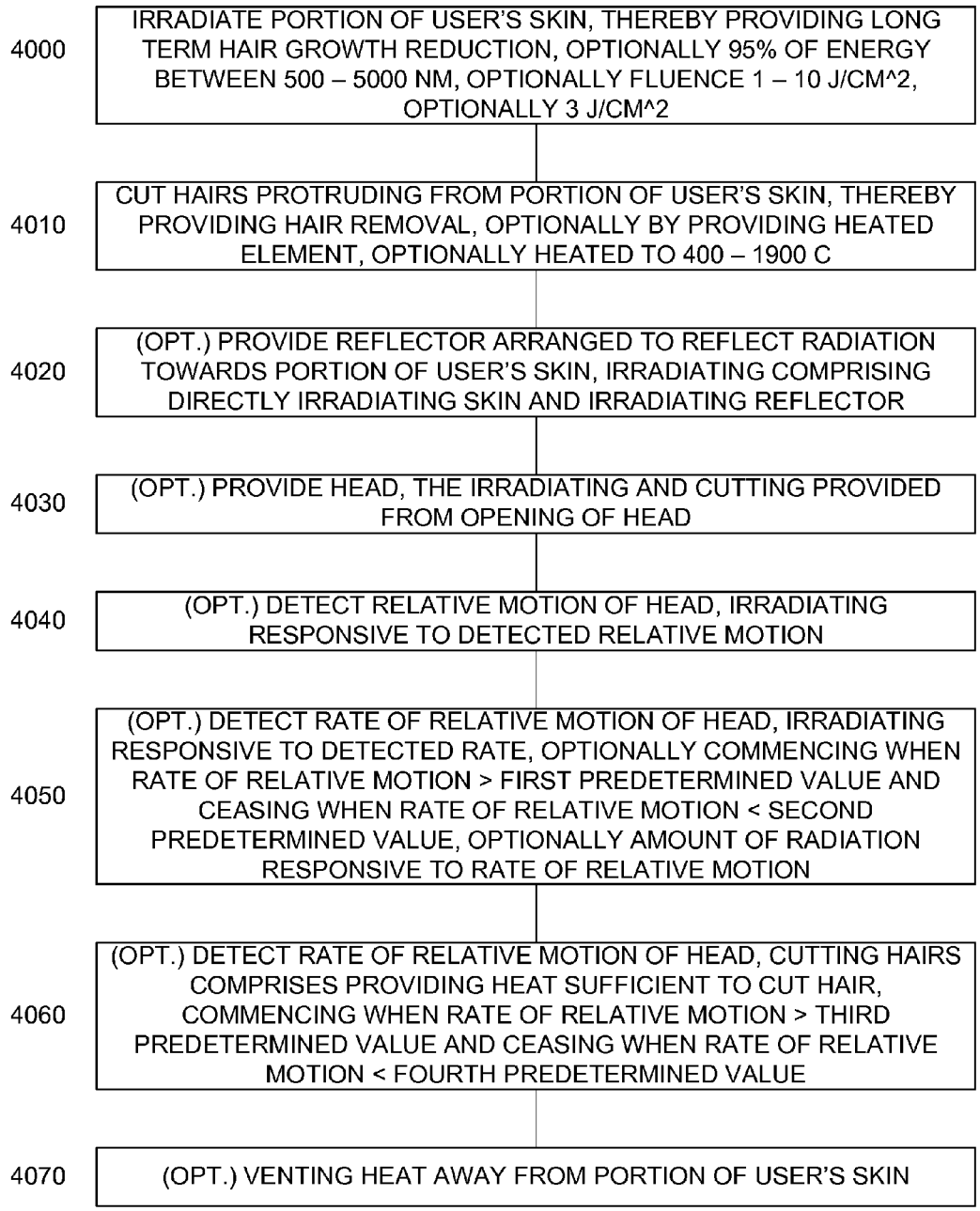
FIG. 12 illustrates a high level flow chart of a method of hair removal and re-growth suppression comprising irradiating a portion of a skin surface and cutting hairs protruding there from, according to certain embodiments.

FIG. 12 illustrates a high level flow chart of a method of hair removal and re-growth suppression comprising irradiating a portion of a skin surface and cutting hairs protruding there from, according to certain embodiments. In stage 4000, a portion of a skin surface is irradiated with EMR. In one embodiment, the EMR exhibits about 95% of its energy within a spectrum of 500-5000 nm, in one particular embodiment, the EMR exhibits less than 10% of its energy within a spectrum of 500-1000 nm. In one embodiment, EMR exhibits about 95% of its energy around a wavelength of 1000 nm. In one embodiment, the fluence of the EMR, measured at the portion of the skin surface, is between 0.5-10 J/CM$^2$, in one further embodiment the fluence being about 3 J/CM$^2$. Advantageously, long term hair regrowth suppression is provided. In one embodiment, the EMR is output by heating an element, as described above in relation to irradiating element 40. In stage 4010, hairs protruding from the portion of the skin surface are cut, thereby providing hair removal. In one embodiment, hairs are cut by providing a heated element. In one embodiment, the temperature of the provided heated element is 400°-1900° C.

In optional stage 4020, a reflector is provided, arranged to substantially reflect radiation towards the portion of the skin surface. In one embodiment, the irradiation of stage 4000 comprises direct irradiation of the portion of the skin surface and irradiating the provided reflector with EMR, the EMR being reflected towards the portion of the skin surface.

In optional stage 4030, a removal and suppression head is provided, the irradiating of stage 4000 and cutting of stage 4010 provided from an opening of the provided removal and suppression head, as described above in relation to removal and suppression head 20. In optional stage 4040, relative motion, or absence thereof, of the provided removal and suppression head of optional stage 4030 in relation to a skin surface to which it is juxtaposed is detected. In one embodiment, the irradiation of stage 4000 is responsive to the detected relative motion. In one embodiment, the irradiation of stage 4000 commences when relative motion of the removal and suppression head is detected and ceased when relative motion is not detected. In optional stage 4050, the rate of relative motion of the provided removal and suppression head of optional stage 4030 is detected. In one embodiment, the irradiation of stage 4000 is responsive to the detected relative motion. In one embodiment, the irradiation commences responsive to a detected rate of relative motion greater than a first predetermined value and ceases responsive to a detected rate of relative motion less than a second predetermined value. In one embodiment, the first predetermined value and the second predetermined value are equal. In one embodiment, the amount of EMR is responsive to the detected rate of relative motion, the amount of EMR increasing responsive to an increase in the detected rate of relative motion and decreasing responsive to a decrease in the detected rate of relative motion.

In optional stage 4060, the rate of relative motion of the provided removal and suppression head of optional stage 4030 is detected. In one embodiment, the cutting of stage 4010 comprises providing electrical energy to a heated element sufficient to cut hair, the heating commencing responsive to a detected rate of relative motion greater than a third predetermined value and ceasing responsive to a detected rate of relative motion less than a fourth predetermined value. In one embodiment, the third predetermined value and the further predetermined value are equal. In optional stage 4070, excess heat is vented away from the portion of the skin surface. In one embodiment, heat is vented by providing at least one heat vent through the provided removal and suppression head of optional stage 4030.

Figure 13:
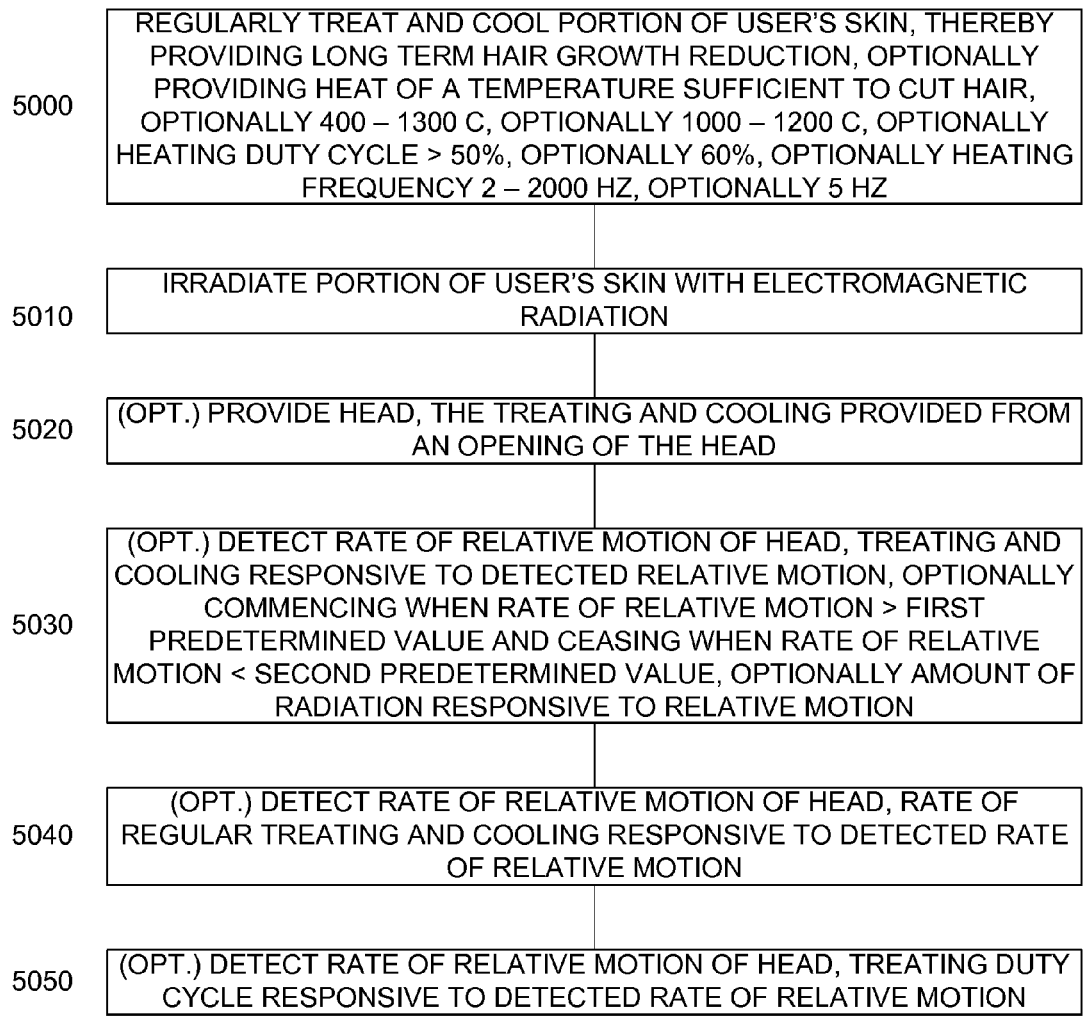
FIG. 13 illustrates a high level flow chart of a method of hair removal and re-growth suppression comprising regularly heating and cooling a portion of a skin surface, according to certain embodiments.

FIG. 13 illustrates a high level flow chart of a method of hair removal and re-growth suppression comprising regularly treating and cooling a portion of a skin surface, according to certain embodiments. In stage 5000, a portion of a skin surface is regularly treated and cooled. In one embodiment, the treating comprises providing heat to the portion of the skin surface. In one embodiment, the provided heat is of a sufficient temperature to cut hair. In one embodiment, the provided heat is between 400°-1900° C., in one particular embodiment the provided heat is 1000°-1900° C. and in one further embodiment the provided heat is about 1900° C. In one embodiment, the heating duty cycle, i.e. the percentage of a period of regular heating and cooling which is heating, is greater than 50%, in one further embodiment the heating duty cycle is about 60%. In one embodiment, the frequency of the regular heating is between 2-2000 Hz, in one further embodiment the frequency being about 5 Hz.

In stage 5010, a portion of the skin surface is irradiated with EMR. In optional stage 5020, a removal and suppression head is provided, the treating and cooling of stage 5000 and the optional irradiating of optional stage 5010 is provided from an opening of the provided removal and suppression head. In optional stage 5030, a rate of relative motion of the provided removal and suppression head of optional stage 5020 in relation to a skin surface to which it is juxtaposed is detected. In one embodiment, the regular treating and cooling of stage 5000 is responsive to the detected rate of relative motion. In one embodiment, the regular treating and cooling commences responsive to a rate of relative motion greater than a first predetermined value and ceases responsive to a rate of relative motion less than a second predetermined value. In one embodiment, the first predetermined value and the second predetermined value are equal. In one embodiment, the amount of EMR provided in stage 5010 is responsive to the detected rate of relative motion. In one embodiment, the amount of EMR is increased responsive to an increase in the detected rate of relative motion and decreased responsive to a decrease in the detected rate of relative motion. In optional stage 5040, a rate of relative motion of the provided removal and suppression head of optional stage 5020 is detected. In one embodiment, the rate of the regular treating and cooling of stage 5000 is responsive to the detected rate of relative motion. In optional stage 5050, a rate of relative motion of the provided removal and suppression head of optional stage 5020 is detected. In one embodiment, the treating duty cycle is responsive to the detected rate of relative motion. In one embodiment, the treating duty cycle increases responsive to an increase in the detected rate of relative motion and decreases responsive to a decrease in the detected rate of relative motion.

Figure 14A:
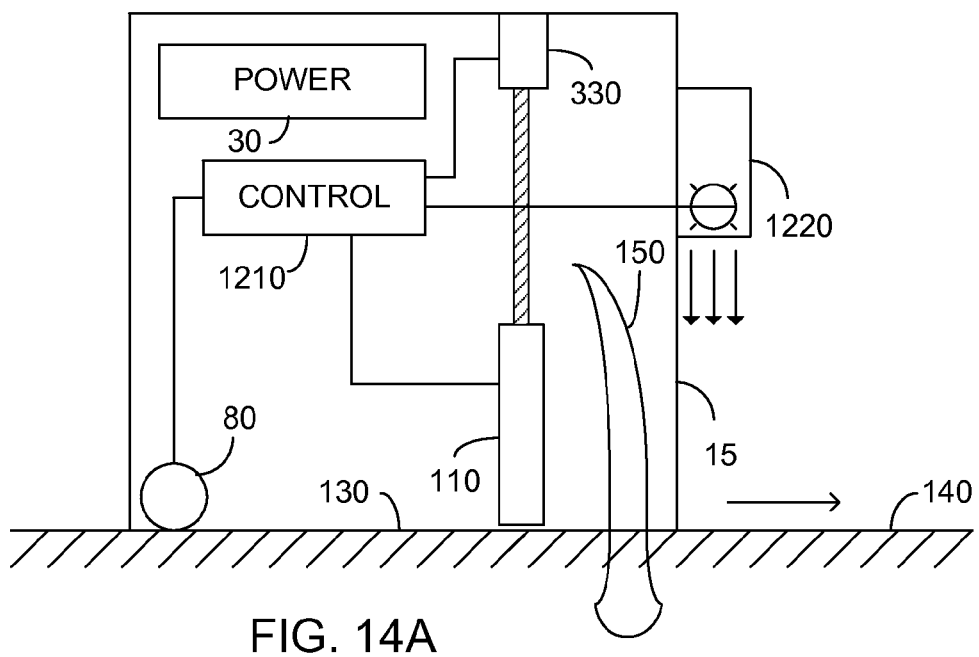
FIG. 14A illustrates a high level side cut view of a hair removal and re-growth suppression apparatus with a cutting element in close proximity to a skin surface so as to shave hair, having an irradiation element.
Figure 14B:
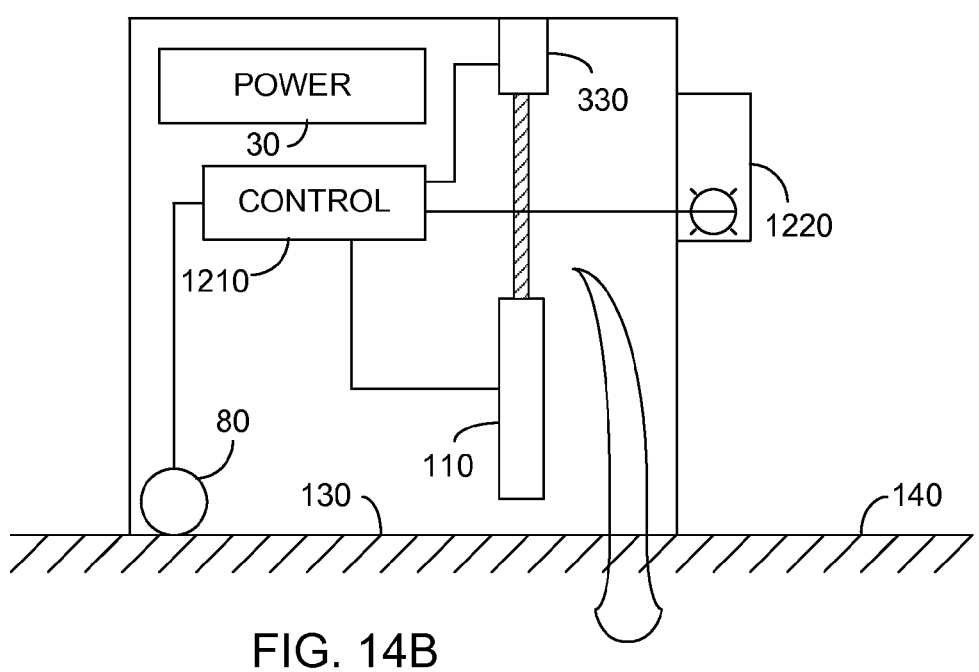
FIG. 14B illustrates a high level side cut view of hair removal and re-growth suppression apparatus of FIG. 14A with the cutting element removed from close proximity to the skin surface.
Figure 14C:
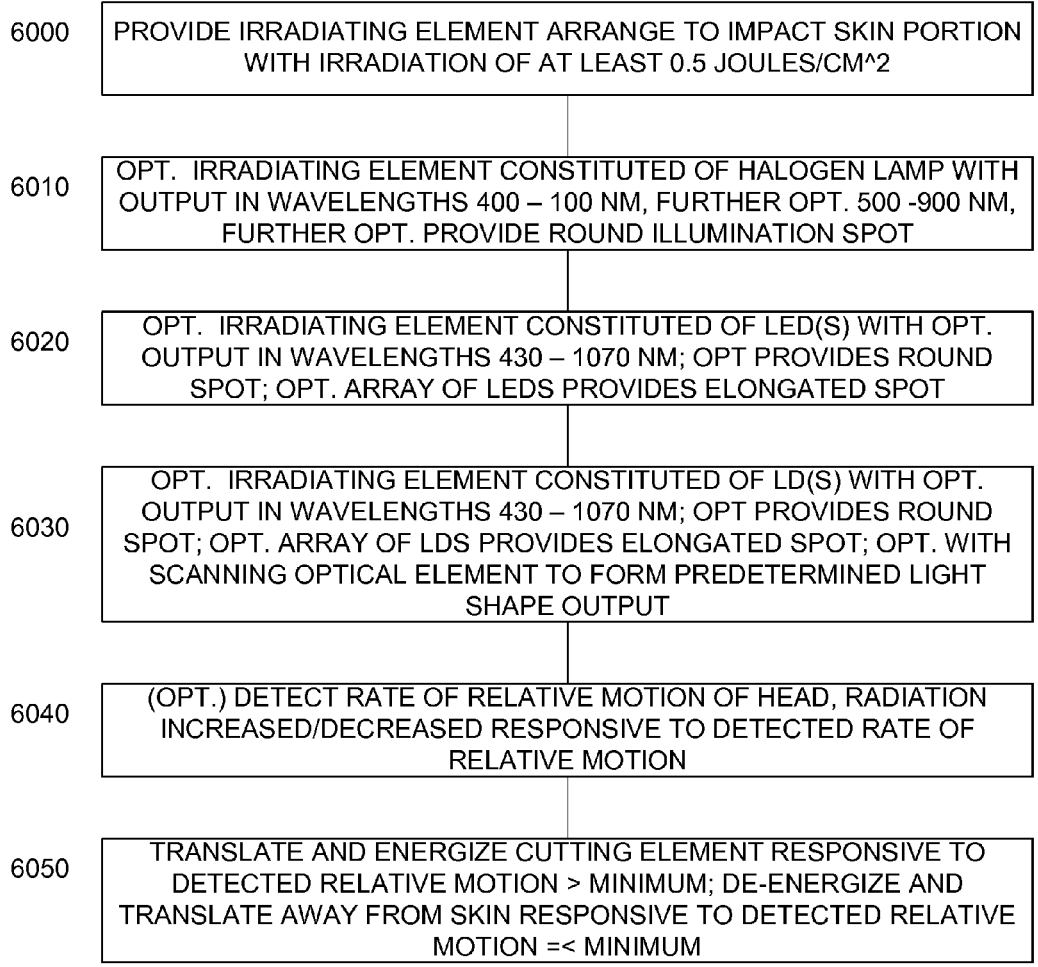
FIG. 14C illustrates certain stages in the operation of hair removal and re-growth suppression apparatus of FIGS. 14A-14B.

FIG. 14A illustrates a high level side cut view of a hair removal and re-growth suppression apparatus 1200 with cutting element 110 in close proximity to skin surface 140 so as to shave hair 150 of skin portion 130; FIG. 14B illustrates a high level side cut view of hair removal and re-growth suppression apparatus 1200 with cutting element 110 removed from close proximity to skin surface 140; and FIG. 14C illustrates certain stages in the operation of hair removal and re-growth suppression apparatus 1200, the drawings being described together for clarity. Hair removal and re-growth suppression apparatus 1200 comprises: housing 15; power source 30; control and driving circuitry 1210; motion sensor 80; cutting element 110; translation mechanism 330; and irradiating element 1220. As described above in relation to the various preceding embodiments, each of power source 30, motion sensor 80, cutting element 110, translation mechanism 330 and irradiating element 1220 are secured in relation to housing 15. Power source 30 provides power for all elements, with connections not shown for simplicity. The output of motion sensor 80 is coupled to an input of control and driving circuitry 1210, a first output of control and driving circuitry 1210 is coupled to translation mechanism 330, a second output of control and driving circuitry 1210 is coupled to the input of cutting element 110 and a third output of control and driving circuitry 1210 is coupled to the input of irradiating element 1220. Hair removal and re-growth suppression apparatus 1200 is juxtaposed with skin portion 130 of skin surface 140. In one non-limiting embodiment translation mechanism 330 comprising a solenoid and a connecting member.

In one embodiment, as described in stage 6000 irradiating element 1220 is a source of light arranged to irradiate a target skin portion just prior to, or just after hair protruding therefrom is shaven by cutting element 110. Preferably, irradiating element 1220 is arranged to irradiate the skin portion with a fluence of at least 0.5 Joules/cm$^2$, the total fluence measured at the portion of the skin surface juxtaposed with hair removal and re-growth suppression apparatus 1200 over the number of passes required to shave any hair 150 protruding from the target skin portion.

In one optional embodiment, as described in stage 6010, irradiating element 1220 is embodied in a broadband halogen lamp, preferably arranged to output light in one or more wavelengths between 400 nanometers and 1100 nanometers. In one further embodiment the predominant wavelength range is 500 nanometers-900 nanometers. In one optional embodiment the output of irradiating element 1220 is arranged to provide a substantially round irradiation zone on the target skin portion.

In one optional embodiment, as described in stage 6020, irradiating element 1220 is embodied in a light emitting diode (LED), preferably arranged to output light in one or more wavelengths between 430 nanometers and 1070 nanometers. In one further embodiment irradiating element 1220 is constituted of a plurality of LEDs formed in an array. In one optional embodiment the output of each constituent LED of irradiating element 1220 is arranged to provide a substantially round irradiation zone on the target skin portion. Thus, in the event of irradiating element 1220 constituted of an array of LEDs, irradiating element 1220 is arranged to provide a substantially elongated irradiation zone on the target skin portion, the elongation being along a single axis.

In one optional embodiment, as described in stage 6030, irradiating element 1220 is embodied in a laser diode (LD), preferably arranged to output radiation in one or more wavelengths between 430 nanometers and 1070 nanometers. In one further embodiment irradiating element 1220 is constituted of a plurality of LDs formed in an array. In one optional embodiment the output of each constituent LD of irradiating element 1220 is arranged to provide a substantially round irradiation zone on the target skin portion. Thus, in the event of irradiating element 1220 constituted of an array of LDs, irradiating element 1220 is arranged to provide a substantially elongated irradiation zone on the target skin portion, the elongation being along a single axis.

In one optional embodiment, as described in stage 6030, irradiating element 1220 is in communication with a scanning optical element arranged to form a predetermined light shape output.

In one optional embodiment, as described in stage 6040, the intensity of irradiation output by irradiating element 1220 is responsive to the amount of motion detected by motion sensor 80. Thus, in the event that motion sensor 80 detects an increased rate of motion in relation to skin surface 140, control and driving circuitry 1210 is arranged to increase the output intensity of irradiating element 1220, and in the event that motion sensor 80 detects a decreased rate of motion in relation to skin surface 140, control and driving circuitry 1210 is arranged to decrease the output intensity of irradiating element 1220 so as to achieve the target luminance of stage 6000.

Responsive to motion sensor 80 detecting relative motion of hair removal and re-growth suppression apparatus 1200 in relation to skin surface 140, control and driving circuitry 1210 is arranged to operate translation mechanism 330 so as to position cutting element 110 adjacent skin surface 140, optionally to a distance of less than 3 mm from skin surface 140, and further energize cutting element 110 with current so as to cut any hair 150 protruding from skin surface 140, as described above and as illustrated in FIG. 14A. In the absence of detected relative motion, or in response to the detected motion being less than a predetermined minimum, control and driving circuitry 1210 is arranged to de-energize cutting element 110 and further operation translation mechanism 330 so as to remove cutting element 110 from the proximity of skin surface 140 as illustrated in FIG. 14B. Control and driving circuitry 1210 is thus arranged to alternately: translate and energize cutting element 110 so as to shave hair 150 and translated and de-energize cutting element 110 so as not to burn skin surface 140. Optionally, as shown in FIG. 14B, the output of irradiating element 1220 is further interrupted so as to prevent continuous irradiation of a particular skin portion 130.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination. In the claims of this application and in the description of the invention, except where the context requires otherwise due to express language or necessary implication, the word "comprise" or variations such as "comprises" or "comprising" is used in any inclusive sense, i.e. to specify the presence of the stated features but not to preclude the presence or addition of further features in various embodiments of the invention.

Unless otherwise defined, all technical and scientific terms used herein have the same meanings as are commonly understood by one of ordinary skill in the art to which this invention belongs. Although methods similar or equivalent to those described herein can be used in the practice or testing of the present invention, suitable methods are described herein.

All publications, patent applications, patents, and other references mentioned herein are incorporated by reference in their entirety. In case of conflict, the patent specification, including definitions, will prevail. In addition, the materials, methods, and examples are illustrative only and not intended to be limiting. No admission is made that any reference constitutes prior art. The discussion of the reference states what their author's assert, and the applicants reserve the right to challenge the accuracy and pertinency of the cited documents. It will be clearly understood that, although a number of prior art complications are referred to herein, this reference does not constitute an admission that any of these documents forms part of the common general knowledge in the art in any country.

It will be appreciated by persons skilled in the art that the present invention is not limited to what has been particularly shown and described hereinabove. Rather the scope of the present invention is defined by the appended claims and includes both combinations and sub-combinations of the various features described hereinabove as well as variations and modifications thereof, which would occur to persons skilled in the art upon reading the foregoing description.

The invention claimed is:

1. A hair shaving apparatus comprising:
    a power source;
    a control circuitry in communication with said power source;
    a housing, an end of said housing arranged to be juxtaposed to a skin surface;
    a motion sensor in communication with said control circuitry and arranged to detect a rate of relative motion of said housing in relation to the skin surface;
    a hair cutting element secured in relation to said housing, said hair cutting element arranged responsive to said control circuitry to be heated to a temperature of at least 400 degrees Celsius, said hair cutting element heated with electric power from said power source responsive to said control circuitry;
    a translation mechanism responsive to said control circuitry and coupled to said hair cutting element and said housing, said translation mechanism arranged to translate said hair cutting element, in relation to said housing end, between a hair shaving position and a retracted position, the hair shaving position closer to the skin surface and said housing end than the retracted position; and
    a radiation source secured to said housing, said radiation source arranged responsive to said control circuitry to provide radiation, said provided radiation arranged to impact the skin surface for which said hair cutting element is arranged to cut hair with a fluence of at least 0.5 Joules/cm2,
    wherein said control circuitry is arranged to:
        responsive to said detected rate of relative motion exceeding a first predetermined limit, enable said radiation source to provide said radiation, and not enable said radiation source to provide said radiation in the absence of said detected rate of relative motion exceeding the first predetermined limit;
        responsive to said detected rate of relative motion exceeding a second predetermined limit, enable said heating of said hair cutting element, and not enable said heating of said hair cutting element in the absence of said detected rate of relative motion exceeding the second predetermined limit, said second predetermined limit greater than said first predetermined limit;
        increase said fluence of said provided radiation responsive to an increase in said detected rate of relative motion and decrease said fluence of said provided radiation responsive to a decrease in said detected rate of relative motion.

2. The hair shaving apparatus according to claim 1, wherein said radiation source is a halogen lamp.

3. The hair shaving apparatus according to claim 2, wherein said halogen lamp is arranged to provide radiation to impact the skin surface with radiation having at least one wavelength between 400 nanometers and 1100 nanometers.

4. The hair shaving apparatus according to claim 2, wherein said halogen lamp is arranged to impact the skin surface with radiation having at least one wavelength between 500 nanometers and 900 nanometers.

5. The hair shaving apparatus according to claim 2, wherein said halogen lamp is arranged to impact the skin surface with radiation having a round illumination spot.

6. The hair shaving apparatus according to claim 1, wherein said radiation source is constituted of at least one light emitting diode (LED).

7. The hair shaving apparatus according to claim 6, wherein said at least one LED is arranged to impact the skin surface with radiation having a round illumination spot.

8. The hair shaving apparatus according to claim 6, wherein said at least one LED is arranged to provide radiation to impact the skin surface with radiation having at least one wavelength between 430 nanometers and 1070 nanometers.

9. The hair shaving apparatus according to claim 6, wherein said radiation source is constitute of a plurality of said LEDs arranged in an array.

10. The hair shaving apparatus according to claim 9, wherein said array of LEDs provide an illumination having an elongated axis on the skin surface.

11. The hair shaving apparatus according to claim 1, wherein said radiation source is constituted of at least one laser diode (LD).

12. The hair shaving apparatus according to claim 11, wherein said at least one LD is arranged to impact the skin surface with radiation having a round illumination spot.

13. The hair shaving apparatus according to claim 11, wherein said at least one LD is arranged to provide radiation to impact the skin surface with radiation having at least one wavelength between 430 nanometers and 1070 nanometers.

14. The hair shaving apparatus according to claim 11, wherein said radiation source is constitute of a plurality of said LDs arranged in an array.

15. The hair shaving apparatus according to claim 14, wherein said array of LDs provide an illumination having an elongated axis on the skin surface.

16. The hair shaving apparatus according to claim 11, wherein said at least one LD is in communication with a scanning optical element arranged to form a predetermined light shape output on the skin surface.

17. The hair shaving apparatus according to claim 1, wherein said hair cutting element is heated to a temperature of 400-1900 degrees Celsius.

18. The hair shaving apparatus according to claim 1, wherein said hair cutting element is heated to a temperature of 1000-1900 degrees Celsius.

19. The hair shaving apparatus according to claim 1, wherein said control circuitry is further arranged, responsive to said detected rate of relative motion exceeding the second predetermined limit, to translate, through said translation mechanism, said hair cutting element from the retracted position to the hair shaving position.

* * * * *